United States Patent
Stevanovic et al.

(10) Patent No.: US 11,352,410 B2
(45) Date of Patent: Jun. 7, 2022

(54) ANTI-KK-LC-1 T CELL RECEPTORS

(71) Applicant: The United States of America, as represented by the Secretary, Department of Health and Human Services, Bethesda, MD (US)

(72) Inventors: Sanja Stevanovic, Bethesda, MD (US); Christian S. Hinrichs, Bethesda, MD (US)

(73) Assignee: The United States of American, as represented by the Secretary, Department of Health and Human Service, Bethesda, MD (US)

( * ) Notice: Subject to any disclaimer, the term of this patent is extended or adjusted under 35 U.S.C. 154(b) by 625 days.

(21) Appl. No.: 16/096,118

(22) PCT Filed: Apr. 17, 2017

(86) PCT No.: PCT/US2017/027865
§ 371 (c)(1),
(2) Date: Oct. 24, 2018

(87) PCT Pub. No.: WO2017/189254
PCT Pub. Date: Nov. 2, 2017

(65) Prior Publication Data
US 2019/0135891 A1    May 9, 2019

Related U.S. Application Data

(60) Provisional application No. 62/327,529, filed on Apr. 26, 2016.

(51) Int. Cl.
| | | |
|---|---|---|
| A61K 39/00 | (2006.01) |
| A61K 39/395 | (2006.01) |
| C07K 16/00 | (2006.01) |
| C07K 16/46 | (2006.01) |
| C07K 14/725 | (2006.01) |
| A61P 35/00 | (2006.01) |
| A61K 35/17 | (2015.01) |
| C12N 15/62 | (2006.01) |
| A61K 38/00 | (2006.01) |

(52) U.S. Cl.
CPC .......... *C07K 14/7051* (2013.01); *A61K 35/17* (2013.01); *A61P 35/00* (2018.01); *C12N 15/62* (2013.01); *A61K 38/00* (2013.01); *C07K 2319/00* (2013.01)

(58) Field of Classification Search
None
See application file for complete search history.

(56) References Cited

U.S. PATENT DOCUMENTS

| 8,034,334 B2 | 10/2011 | Dudley et al. |
| 8,383,099 B2 | 2/2013 | Dudley et al. |
| 2012/0244133 A1 | 9/2012 | Rosenberg et al. |

FOREIGN PATENT DOCUMENTS

| WO | WO 99/03995 A1 | 1/1999 | |
| WO | WO 2007/131092 A2 | 11/2007 | |
| WO | WO 2010/087335 A1 | 8/2010 | |
| WO | WO-2010088160 A1 * | 8/2010 | ............... A61P 35/00 |
| WO | WO 2012/040012 A1 | 3/2012 | |
| WO | WO 2013/039889 A1 | 3/2013 | |
| WO | WO 2015/009606 A1 | 1/2015 | |
| WO | WO 2015/014375 A1 | 2/2015 | |
| WO | WO 2015/014869 A1 | 2/2015 | |
| WO | WO 2017/089756 A1 | 6/2017 | |
| WO | WO-2017089756 A1 * | 6/2017 | ............... A61P 35/00 |

OTHER PUBLICATIONS

Brawley et al. Complementarity-Determining Region 1 Sequence Requirements Drive Limited Vα Usage in Response to Influenza Hemagglutinin 307-319 Peptide. J Immunol Apr. 15, 2002, 168 (8) 3894-3901. (Year: 2002).*

Kieke et al. Selection of functional T cell receptor mutants from a yeast surface-display library. Proc Natl Acad Sci U S A. May 11, 1999; 96(10): 5651-5656. (Year: 1999).*

Aggen et al. Identification and engineering of human variable regions that allow expression of stable single-chain T cell receptors . Protein Engineering, Design and Selection, vol. 24, Issue 4, Apr. 2011, pp. 361-372. (Year: 2011).*

Adams et al., "HLA class I and II genotype of the NCI-60 cell lines," *J. Transl. Med.*, 3(1):11 (2005).

Cohen et al., "Enhanced Antitumor Activity of Murine-Human Hybrid T-Cell Receptor (TCR) in Human Lymphocytes is Associated with Improved Pairing and TCR/CD3 Stability," *Cancer Res.*, 66(17): 8878-8886 (2006).

Cohen et al., "Enhanced Antitumor Activity of T Cells Engineered to Express T-Cell Receptors with a Second Disulfide Bond," *Cancer Res.*, 67(8): 3898-3903 (2007).

Dudley et al., "Generation of Tumor-Infiltrating Lymphocyte Cultures for Use in Adoptive Transfer Therapy for Melanoma Patients," *J. Immunother.*, 26:332-342 (2003).

Fukuyama et al., "Identification of a New Cancer/Germline Gene, KK-LC-1, Encoding an Antigen Recognized by Autologous CTL Induced on Human Lung Adenocarcinoma," *Cancer Res.*, 66(9): 4922-4928 (2006).

(Continued)

*Primary Examiner* — Maher M Haddad
(74) *Attorney, Agent, or Firm* — Leydig, Voit & Mayer

(57) ABSTRACT

Disclosed is an isolated or purified T cell receptor (TCR) having antigenic specificity for Kita-Kyushu Lung Cancer Antigen $1_{52-60}$ (KK-LC-$1_{52-60}$). Related polypeptides and proteins, as well as related nucleic acids, recombinant expression vectors, host cells, populations of cells, and pharmaceutical compositions are also provided. Also disclosed are methods of detecting the presence of cancer in a mammal and methods of treating or preventing cancer in a mammal.

26 Claims, 9 Drawing Sheets

Specification includes a Sequence Listing.

(56) References Cited

OTHER PUBLICATIONS

Haga-Friedman et al., "Incorporation of Transmembrane Hydrophobic Mutations in the TCR Enhance Its Surface Expression and T Cell Functional Avidity," *J. Immunol.*, 188: 5538-5546 (2012).

Hanagiri et al., "Antitumor activity of human γδ T cells transducted with CD8 and with T-cell receptors of tumor-specific cytotoxic T lymphocytes," *Cancer Sci.*, 103(8): 1414-1419 (2012).

Hanagiri et al., "Retraction statement: Antitumor activity of human γδ T cells transducted with CDS and with T-cell receptors of tumorspecific cytotoxic T" *Cancer Sci.*, 105(1): 141 (2014).

International Bureau, International Search Report and Written Opinion in International Application No. PCT/US2017/027865, dated Aug. 25, 2017.

Lundegaard et al., "NetMHC-3.0: accurate web accessible predictions of human, mouse and monkey MHC class I affinities for peptides of length 8-11" *Nucleic Acids Res.*, 36: W509-512 (2008).

Nielsen et al., "Reliable prediction of T-cell epitopes using neural networks with novel sequence representations," *Protein Sci.*, 12: 1007-1017 (2003).

Paret et al., "CXorf61 is a target for T cell based immunotherapy of triplenegative breast cancer," *Oncotarget*, 6(28): 25356-25367 (2015).

Riddell et al., "The use of anti-CD3 and anti-CD28 monoclonal antibodies to clone and expand human antigen-specific T cells," *J. Immunol. Methods*, 128:189-201 (1990).

Szymczak et al., "Correction of multi-gene deficiency in vivo using a single 'self-cleaving' 2A peptide-based retroviral vector," *Nat. Biotechnol.*, 22(5):589-594 (2004).

Murphy et al., "T-cell receptors concentrate diversity in the third hypervariable region," *Janeway's Immunobiology, 7th Edition*, p. 157-158 (2008).

"TRA T-cell receptor alpha locus [*Homo sapiens* (human)]," Gene ID: 6955, (updated Oct. 9, 2016), Entrez Gene (ncbi.nlm.nih.gov/gene), printed on Dec. 8, 2016.

"TRB T cell receptor beta locus [*Homo sapiens* (human)]," Gene ID: 6957, (updated Oct. 9, 2016), Entrez Gene (ncbi.nlm.nih.gov/gene), printed on Dec. 8, 2016.

* cited by examiner

SEQUENCE LISTING

```
<160> NUMBER OF SEQ ID NOS: 62

<210> SEQ ID NO 1
<211> LENGTH: 113
<212> TYPE: PRT
<213> ORGANISM: Homo sapiens

<400> SEQUENCE: 1

Met Asn Phe Tyr Leu Leu Leu Ala Ser Ser Ile Leu Cys Ala Leu Ile
1               5                   10                  15

Val Phe Trp Lys Tyr Arg Arg Phe Gln Arg Asn Thr Gly Glu Met Ser
            20                  25                  30

Ser Asn Ser Thr Ala Leu Ala Leu Val Arg Pro Ser Ser Ser Gly Leu
        35                  40                  45

Ile Asn Ser Asn Thr Asp Asn Asn Leu Ala Val Tyr Asp Leu Ser Arg
    50                  55                  60

Asp Ile Leu Asn Asn Phe Pro His Ser Ile Ala Arg Gln Lys Arg Ile
65                  70                  75                  80

Leu Val Asn Leu Ser Met Val Glu Asn Lys Leu Val Glu Leu Glu His
                85                  90                  95

Thr Leu Leu Ser Lys Gly Phe Arg Gly Ala Ser Pro His Arg Lys Ser
                100                 105                 110

Thr

<210> SEQ ID NO 2
<211> LENGTH: 9
<212> TYPE: PRT
<213> ORGANISM: Homo sapiens

<400> SEQUENCE: 2
```

Asn Thr Asp Asn Asn Leu Ala Val Tyr
1               5

<210> SEQ ID NO 3
<211> LENGTH: 5
<212> TYPE: PRT
<213> ORGANISM: Homo sapiens

<400> SEQUENCE: 3

Ser Ile Phe Asn Thr
1               5

<210> SEQ ID NO 4
<211> LENGTH: 7
<212> TYPE: PRT
<213> ORGANISM: Homo sapiens

<400> SEQUENCE: 4

Leu Tyr Lys Ala Gly Glu Leu
1               5

<210> SEQ ID NO 5
<211> LENGTH: 11
<212> TYPE: PRT
<213> ORGANISM: Homo sapiens

<400> SEQUENCE: 5

Ala Gly Gln Leu Val Tyr Gly Asn Lys Leu Val
1               5                   10

<210> SEQ ID NO 6
<211> LENGTH: 5
<212> TYPE: PRT
<213> ORGANISM: Homo sapiens

<400> SEQUENCE: 6

Ser Gly His Thr Ala
1               5

<210> SEQ ID NO 7
<211> LENGTH: 6
<212> TYPE: PRT
<213> ORGANISM: Homo sapiens

<400> SEQUENCE: 7

Phe Gln Gly Thr Gly Ala
1               5

<210> SEQ ID NO 8
<211> LENGTH: 13
<212> TYPE: PRT
<213> ORGANISM: Homo sapiens

<400> SEQUENCE: 8

Ala Ser Ser Leu Gly Thr Gly Gly Tyr Asn Glu Gln Phe
1               5                   10

<210> SEQ ID NO 9
<211> LENGTH: 129
<212> TYPE: PRT
<213> ORGANISM: Homo sapiens

<400> SEQUENCE: 9

Met Leu Leu Glu His Leu Leu Ile Ile Leu Trp Met Gln Leu Thr Trp

-continued

```
                1               5                  10                 15
Val Ser Gly Gln Gln Leu Asn Gln Ser Pro Gln Ser Met Phe Ile Gln
            20                 25                 30

Glu Gly Glu Asp Val Ser Met Asn Cys Thr Ser Ser Ile Phe Asn
            35                 40                 45

Thr Trp Leu Trp Tyr Lys Gln Glu Pro Gly Glu Pro Val Leu Leu
    50                 55                 60

Ile Ala Leu Tyr Lys Ala Gly Glu Leu Thr Ser Asn Gly Arg Leu Thr
65                 70                 75                 80

Ala Gln Phe Gly Ile Thr Arg Lys Asp Ser Phe Leu Asn Ile Ser Ala
                85                 90                 95

Ser Ile Pro Ser Asp Val Gly Ile Tyr Phe Cys Ala Gly Gln Leu Val
                100                105                110

Tyr Gly Asn Lys Leu Val Phe Gly Ala Gly Thr Ile Leu Arg Val Lys
                115                120                125

Ser
```

<210> SEQ ID NO 10
<211> LENGTH: 134
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Ala or Gly

<400> SEQUENCE: 10

```
Met Xaa Thr Arg Leu Leu Cys Trp Ala Ala Leu Cys Leu Leu Gly Ala
1               5                  10                 15

Asp His Thr Gly Ala Gly Val Ser Gln Thr Pro Ser Asn Lys Val Thr
            20                 25                 30

Glu Lys Gly Lys Tyr Val Glu Leu Arg Cys Asp Pro Ile Ser Gly His
            35                 40                 45

Thr Ala Leu Tyr Trp Tyr Arg Gln Ser Leu Gly Gln Gly Pro Glu Phe
    50                 55                 60

Leu Ile Tyr Phe Gln Gly Thr Gly Ala Ala Asp Asp Ser Gly Leu Pro
65                 70                 75                 80

Asn Asp Arg Phe Phe Ala Val Arg Pro Glu Gly Ser Val Ser Thr Leu
                85                 90                 95

Lys Ile Gln Arg Thr Glu Arg Gly Asp Ser Ala Val Tyr Leu Cys Ala
                100                105                110

Ser Ser Leu Gly Thr Gly Gly Tyr Asn Glu Gln Phe Phe Gly Pro Gly
                115                120                125

Thr Arg Leu Thr Val Leu
    130
```

<210> SEQ ID NO 11
<211> LENGTH: 134
<212> TYPE: PRT
<213> ORGANISM: Homo sapiens

<400> SEQUENCE: 11

```
Met Gly Thr Arg Leu Leu Cys Trp Ala Ala Leu Cys Leu Leu Gly Ala
1               5                  10                 15

Asp His Thr Gly Ala Gly Val Ser Gln Thr Pro Ser Asn Lys Val Thr
            20                 25                 30
```

```
Glu Lys Gly Lys Tyr Val Glu Leu Arg Cys Asp Pro Ile Ser Gly His
            35                  40                  45
Thr Ala Leu Tyr Trp Tyr Arg Gln Ser Leu Gly Gln Gly Pro Glu Phe
 50                  55                  60
Leu Ile Tyr Phe Gln Gly Thr Gly Ala Ala Asp Asp Ser Gly Leu Pro
 65                  70                  75                  80
Asn Asp Arg Phe Phe Ala Val Arg Pro Glu Gly Ser Val Ser Thr Leu
                85                  90                  95
Lys Ile Gln Arg Thr Glu Arg Gly Asp Ser Ala Val Tyr Leu Cys Ala
            100                 105                 110
Ser Ser Leu Gly Thr Gly Gly Tyr Asn Glu Gln Phe Phe Gly Pro Gly
            115                 120                 125
Thr Arg Leu Thr Val Leu
            130
```

<210> SEQ ID NO 12
<211> LENGTH: 600
<212> TYPE: PRT
<213> ORGANISM: Artificial Sequence
<220> FEATURE:
<223> OTHER INFORMATION: Synthetic

<400> SEQUENCE: 12

```
Met Ala Thr Arg Leu Leu Cys Trp Ala Ala Leu Cys Leu Leu Gly Ala
 1               5                  10                  15
Asp His Thr Gly Ala Gly Val Ser Gln Thr Pro Ser Asn Lys Val Thr
            20                  25                  30
Glu Lys Gly Lys Tyr Val Glu Leu Arg Cys Asp Pro Ile Ser Gly His
            35                  40                  45
Thr Ala Leu Tyr Trp Tyr Arg Gln Ser Leu Gly Gln Gly Pro Glu Phe
 50                  55                  60
Leu Ile Tyr Phe Gln Gly Thr Gly Ala Ala Asp Asp Ser Gly Leu Pro
 65                  70                  75                  80
Asn Asp Arg Phe Phe Ala Val Arg Pro Glu Gly Ser Val Ser Thr Leu
                85                  90                  95
Lys Ile Gln Arg Thr Glu Arg Gly Asp Ser Ala Val Tyr Leu Cys Ala
            100                 105                 110
Ser Ser Leu Gly Thr Gly Gly Tyr Asn Glu Gln Phe Phe Gly Pro Gly
            115                 120                 125
Thr Arg Leu Thr Val Leu Glu Asp Leu Arg Asn Val Thr Pro Pro Lys
            130                 135                 140
Val Ser Leu Phe Glu Pro Ser Lys Ala Glu Ile Ala Asn Lys Gln Lys
145                 150                 155                 160
Ala Thr Leu Val Cys Leu Ala Arg Gly Phe Phe Pro Asp His Val Glu
                165                 170                 175
Leu Ser Trp Trp Val Asn Gly Lys Glu Val His Ser Gly Val Cys Thr
            180                 185                 190
Asp Pro Gln Ala Tyr Lys Glu Ser Asn Tyr Ser Tyr Cys Leu Ser Ser
            195                 200                 205
Arg Leu Arg Val Ser Ala Thr Phe Trp His Asn Pro Arg Asn His Phe
            210                 215                 220
Arg Cys Gln Val Gln Phe His Gly Leu Ser Glu Glu Asp Lys Trp Pro
225                 230                 235                 240
Glu Gly Ser Pro Lys Pro Val Thr Gln Asn Ile Ser Ala Glu Ala Trp
                245                 250                 255
```

Gly Arg Ala Asp Cys Gly Ile Thr Ser Ala Ser Tyr Gln Gln Gly Val
            260                 265                 270

Leu Ser Ala Thr Ile Leu Tyr Glu Ile Leu Gly Lys Ala Thr Leu
275                 280                 285

Tyr Ala Val Leu Val Ser Thr Leu Val Val Met Ala Met Val Lys Arg
290                 295                 300

Lys Asn Ser Arg Ala Lys Arg Ser Gly Ser Gly Ala Thr Asn Phe Ser
305                 310                 315                 320

Leu Leu Lys Gln Ala Gly Asp Val Glu Glu Asn Pro Gly Pro Met Leu
            325                 330                 335

Leu Glu His Leu Leu Ile Ile Leu Trp Met Gln Leu Thr Trp Val Ser
            340                 345                 350

Gly Gln Gln Leu Asn Gln Ser Pro Gln Ser Met Phe Ile Gln Glu Gly
            355                 360                 365

Glu Asp Val Ser Met Asn Cys Thr Ser Ser Ser Ile Phe Asn Thr Trp
370                 375                 380

Leu Trp Tyr Lys Gln Glu Pro Gly Glu Gly Pro Val Leu Leu Ile Ala
385                 390                 395                 400

Leu Tyr Lys Ala Gly Glu Leu Thr Ser Asn Gly Arg Leu Thr Ala Gln
            405                 410                 415

Phe Gly Ile Thr Arg Lys Asp Ser Phe Leu Asn Ile Ser Ala Ser Ile
            420                 425                 430

Pro Ser Asp Val Gly Ile Tyr Phe Cys Ala Gly Gln Leu Val Tyr Gly
            435                 440                 445

Asn Lys Leu Val Phe Gly Ala Gly Thr Ile Leu Arg Val Lys Ser Asn
450                 455                 460

Ile Gln Asn Pro Glu Pro Ala Val Tyr Gln Leu Lys Asp Pro Arg Ser
465                 470                 475                 480

Gln Asp Ser Thr Leu Cys Leu Phe Thr Asp Phe Asp Ser Gln Ile Asn
            485                 490                 495

Val Pro Lys Thr Met Glu Ser Gly Thr Phe Ile Thr Asp Lys Cys Val
            500                 505                 510

Leu Asp Met Lys Ala Met Asp Ser Lys Ser Asn Gly Ala Ile Ala Trp
            515                 520                 525

Ser Asn Gln Thr Ser Phe Thr Cys Gln Asp Ile Phe Lys Glu Thr Asn
530                 535                 540

Ala Thr Tyr Pro Ser Ser Asp Val Pro Cys Asp Ala Thr Leu Thr Glu
545                 550                 555                 560

Lys Ser Phe Glu Thr Asp Met Asn Leu Asn Phe Gln Asn Leu Leu Val
            565                 570                 575

Ile Val Leu Arg Ile Leu Leu Leu Lys Val Ala Gly Phe Asn Leu Leu
            580                 585                 590

Met Thr Leu Arg Leu Trp Ser Ser
            595                 600

<210> SEQ ID NO 13
<211> LENGTH: 137
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (48)..(48)
<223> OTHER INFORMATION: X is Thr or Cys
<220> FEATURE:

```
<221> NAME/KEY: MISC_FEATURE
<222> LOCATION: (112)..(112)
<223> OTHER INFORMATION: X is Ser, Gly, Ala, Val, Leu, Ile, Pro, Phe,
      Met, or Trp
<220> FEATURE:
<221> NAME/KEY: MISC_FEATURE
<222> LOCATION: (114)..(114)
<223> OTHER INFORMATION: X is Met, Gly, Ala, Val, Leu, Ile, Pro, Phe,
      Met, or Trp
<220> FEATURE:
<221> NAME/KEY: MISC_FEATURE
<222> LOCATION: (115)..(115)
<223> OTHER INFORMATION: X is Gly, Ala, Val, Leu, Ile, Pro, Phe, Met, or
      Trp

<400> SEQUENCE: 13
```

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Ser Gln Ile
            20                  25                  30

Asn Val Pro Lys Thr Met Glu Ser Gly Thr Phe Ile Thr Asp Lys Xaa
                35                  40                  45

Val Leu Asp Met Lys Ala Met Asp Ser Lys Ser Asn Gly Ala Ile Ala
50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Xaa
            100                 105                 110

Val Xaa Xaa Leu Arg Ile Leu Leu Leu Lys Val Ala Gly Phe Asn Leu
        115                 120                 125

Leu Met Thr Leu Arg Leu Trp Ser Ser
    130                 135

```
<210> SEQ ID NO 14
<211> LENGTH: 173
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (57)..(57)
<223> OTHER INFORMATION: X is Ser or Cys

<400> SEQUENCE: 14
```

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
            35                  40                  45

Gly Lys Glu Val His Ser Gly Val Xaa Thr Asp Pro Gln Ala Tyr Lys
50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
            115                 120                 125

Ile Thr Ser Ala Ser Tyr Gln Gln Gly Val Leu Ser Ala Thr Ile Leu
        130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

<210> SEQ ID NO 15
<211> LENGTH: 266
<212> TYPE: PRT
<213> ORGANISM: Artificial Sequence
<220> FEATURE:
<223> OTHER INFORMATION: Synthetic

<400> SEQUENCE: 15

Met Leu Leu Glu His Leu Leu Ile Ile Leu Trp Met Gln Leu Thr Trp
1               5                   10                  15

Val Ser Gly Gln Gln Leu Asn Gln Ser Pro Gln Ser Met Phe Ile Gln
            20                  25                  30

Glu Gly Glu Asp Val Ser Met Asn Cys Thr Ser Ser Ser Ile Phe Asn
        35                  40                  45

Thr Trp Leu Trp Tyr Lys Gln Glu Pro Gly Glu Gly Pro Val Leu Leu
    50                  55                  60

Ile Ala Leu Tyr Lys Ala Gly Glu Leu Thr Ser Asn Gly Arg Leu Thr
65                  70                  75                  80

Ala Gln Phe Gly Ile Thr Arg Lys Asp Ser Phe Leu Asn Ile Ser Ala
                85                  90                  95

Ser Ile Pro Ser Asp Val Gly Ile Tyr Phe Cys Ala Gly Gln Leu Val
            100                 105                 110

Tyr Gly Asn Lys Leu Val Phe Gly Ala Gly Thr Ile Leu Arg Val Lys
        115                 120                 125

Ser Asn Ile Gln Asn Pro Glu Pro Ala Val Tyr Gln Leu Lys Asp Pro
    130                 135                 140

Arg Ser Gln Asp Ser Thr Leu Cys Leu Phe Thr Asp Phe Asp Ser Gln
145                 150                 155                 160

Ile Asn Val Pro Lys Thr Met Glu Ser Gly Thr Phe Ile Thr Asp Lys
                165                 170                 175

Cys Val Leu Asp Met Lys Ala Met Asp Ser Lys Ser Asn Gly Ala Ile
            180                 185                 190

Ala Trp Ser Asn Gln Thr Ser Phe Thr Cys Gln Asp Ile Phe Lys Glu
        195                 200                 205

Thr Asn Ala Thr Tyr Pro Ser Ser Asp Val Pro Cys Asp Ala Thr Leu
    210                 215                 220

Thr Glu Lys Ser Phe Glu Thr Asp Met Asn Leu Asn Phe Gln Asn Leu
225                 230                 235                 240

Leu Val Ile Val Leu Arg Ile Leu Leu Leu Lys Val Ala Gly Phe Asn
                245                 250                 255

Leu Leu Met Thr Leu Arg Leu Trp Ser Ser
            260                 265

<210> SEQ ID NO 16
<211> LENGTH: 307
<212> TYPE: PRT
<213> ORGANISM: Artificial Sequence
<220> FEATURE:

<223> OTHER INFORMATION: Synthetic

<400> SEQUENCE: 16

Met Ala Thr Arg Leu Leu Cys Trp Ala Ala Leu Cys Leu Leu Gly Ala
1               5                   10                  15

Asp His Thr Gly Ala Gly Val Ser Gln Thr Pro Ser Asn Lys Val Thr
            20                  25                  30

Glu Lys Gly Lys Tyr Val Glu Leu Arg Cys Asp Pro Ile Ser Gly His
        35                  40                  45

Thr Ala Leu Tyr Trp Tyr Arg Gln Ser Leu Gly Gln Gly Pro Glu Phe
    50                  55                  60

Leu Ile Tyr Phe Gln Gly Thr Gly Ala Ala Asp Asp Ser Gly Leu Pro
65                  70                  75                  80

Asn Asp Arg Phe Phe Ala Val Arg Pro Glu Gly Ser Val Ser Thr Leu
                85                  90                  95

Lys Ile Gln Arg Thr Glu Arg Gly Asp Ser Ala Val Tyr Leu Cys Ala
            100                 105                 110

Ser Ser Leu Gly Thr Gly Gly Tyr Asn Glu Gln Phe Phe Gly Pro Gly
        115                 120                 125

Thr Arg Leu Thr Val Leu Glu Asp Leu Arg Asn Val Thr Pro Pro Lys
    130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Cys Thr
            180                 185                 190

Asp Pro Gln Ala Tyr Lys Glu Ser Asn Tyr Ser Tyr Cys Leu Ser Ser
        195                 200                 205

Arg Leu Arg Val Ser Ala Thr Phe Trp His Asn Pro Arg Asn His Phe
    210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Thr Leu Val Val Met Ala Met Val Lys Arg
    290                 295                 300

Lys Asn Ser
305

<210> SEQ ID NO 17
<211> LENGTH: 27
<212> TYPE: PRT
<213> ORGANISM: Artificial Sequence
<220> FEATURE:
<223> OTHER INFORMATION: Synthetic

<400> SEQUENCE: 17

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25

```
<210> SEQ ID NO 18
<211> LENGTH: 13
<212> TYPE: PRT
<213> ORGANISM: Homo sapiens

<400> SEQUENCE: 18

Cys Ala Gly Gln Leu Val Tyr Gly Asn Lys Leu Val Phe
1               5                   10

<210> SEQ ID NO 19
<211> LENGTH: 15
<212> TYPE: PRT
<213> ORGANISM: Homo sapiens

<400> SEQUENCE: 19

Cys Ala Ser Ser Leu Gly Thr Gly Gly Tyr Asn Glu Gln Phe Phe
1               5                   10                  15

<210> SEQ ID NO 20
<211> LENGTH: 15
<212> TYPE: PRT
<213> ORGANISM: Homo sapiens

<400> SEQUENCE: 20

Met Asn Phe Tyr Leu Leu Leu Ala Ser Ser Ile Leu Cys Ala Leu
1               5                   10                  15

<210> SEQ ID NO 21
<211> LENGTH: 15
<212> TYPE: PRT
<213> ORGANISM: Homo sapiens

<400> SEQUENCE: 21

Leu Leu Leu Ala Ser Ser Ile Leu Cys Ala Leu Ile Val Phe Trp
1               5                   10                  15

<210> SEQ ID NO 22
<211> LENGTH: 15
<212> TYPE: PRT
<213> ORGANISM: Homo sapiens

<400> SEQUENCE: 22

Ser Ser Ile Leu Cys Ala Leu Ile Val Phe Trp Lys Tyr Arg Arg
1               5                   10                  15

<210> SEQ ID NO 23
<211> LENGTH: 15
<212> TYPE: PRT
<213> ORGANISM: Homo sapiens

<400> SEQUENCE: 23

Cys Ala Leu Ile Val Phe Trp Lys Tyr Arg Arg Phe Gln Arg Asn
1               5                   10                  15

<210> SEQ ID NO 24
<211> LENGTH: 15
<212> TYPE: PRT
<213> ORGANISM: Homo sapiens

<400> SEQUENCE: 24

Val Phe Trp Lys Tyr Arg Arg Phe Gln Arg Asn Thr Gly Glu Met
1               5                   10                  15
```

```
<210> SEQ ID NO 25
<211> LENGTH: 15
<212> TYPE: PRT
<213> ORGANISM: Homo sapiens

<400> SEQUENCE: 25

Tyr Arg Arg Phe Gln Arg Asn Thr Gly Glu Met Ser Ser Asn Ser
1               5                   10                  15

<210> SEQ ID NO 26
<211> LENGTH: 15
<212> TYPE: PRT
<213> ORGANISM: Homo sapiens

<400> SEQUENCE: 26

Gln Arg Asn Thr Gly Glu Met Ser Ser Asn Ser Thr Ala Leu Ala
1               5                   10                  15

<210> SEQ ID NO 27
<211> LENGTH: 15
<212> TYPE: PRT
<213> ORGANISM: Homo sapiens

<400> SEQUENCE: 27

Gly Glu Met Ser Ser Asn Ser Thr Ala Leu Ala Leu Val Arg Pro
1               5                   10                  15

<210> SEQ ID NO 28
<211> LENGTH: 15
<212> TYPE: PRT
<213> ORGANISM: Homo sapiens

<400> SEQUENCE: 28

Ser Asn Ser Thr Ala Leu Ala Leu Val Arg Pro Ser Ser Ser Gly
1               5                   10                  15

<210> SEQ ID NO 29
<211> LENGTH: 15
<212> TYPE: PRT
<213> ORGANISM: Homo sapiens

<400> SEQUENCE: 29

Ala Leu Ala Leu Val Arg Pro Ser Ser Ser Gly Leu Ile Asn Ser
1               5                   10                  15

<210> SEQ ID NO 30
<211> LENGTH: 15
<212> TYPE: PRT
<213> ORGANISM: Homo sapiens

<400> SEQUENCE: 30

Val Arg Pro Ser Ser Ser Gly Leu Ile Asn Ser Asn Thr Asp Asn
1               5                   10                  15

<210> SEQ ID NO 31
<211> LENGTH: 15
<212> TYPE: PRT
<213> ORGANISM: Homo sapiens

<400> SEQUENCE: 31

Ser Ser Gly Leu Ile Asn Ser Asn Thr Asp Asn Asn Leu Ala Val
1               5                   10                  15

<210> SEQ ID NO 32
<211> LENGTH: 15
```

-continued

```
<212> TYPE: PRT
<213> ORGANISM: Homo sapiens

<400> SEQUENCE: 32

Ile Asn Ser Asn Thr Asp Asn Asn Leu Ala Val Tyr Asp Leu Ser
1               5                   10                  15

<210> SEQ ID NO 33
<211> LENGTH: 15
<212> TYPE: PRT
<213> ORGANISM: Homo sapiens

<400> SEQUENCE: 33

Thr Asp Asn Asn Leu Ala Val Tyr Asp Leu Ser Arg Asp Ile Leu
1               5                   10                  15

<210> SEQ ID NO 34
<211> LENGTH: 15
<212> TYPE: PRT
<213> ORGANISM: Homo sapiens

<400> SEQUENCE: 34

Leu Ala Val Tyr Asp Leu Ser Arg Asp Ile Leu Asn Asn Phe Pro
1               5                   10                  15

<210> SEQ ID NO 35
<211> LENGTH: 15
<212> TYPE: PRT
<213> ORGANISM: Homo sapiens

<400> SEQUENCE: 35

Asp Leu Ser Arg Asp Ile Leu Asn Asn Phe Pro His Ser Ile Ala
1               5                   10                  15

<210> SEQ ID NO 36
<211> LENGTH: 15
<212> TYPE: PRT
<213> ORGANISM: Homo sapiens

<400> SEQUENCE: 36

Asp Ile Leu Asn Asn Phe Pro His Ser Ile Ala Arg Gln Lys Arg
1               5                   10                  15

<210> SEQ ID NO 37
<211> LENGTH: 15
<212> TYPE: PRT
<213> ORGANISM: Homo sapiens

<400> SEQUENCE: 37

Asn Phe Pro His Ser Ile Ala Arg Gln Lys Arg Ile Leu Val Asn
1               5                   10                  15

<210> SEQ ID NO 38
<211> LENGTH: 15
<212> TYPE: PRT
<213> ORGANISM: Homo sapiens

<400> SEQUENCE: 38

Ser Ile Ala Arg Gln Lys Arg Ile Leu Val Asn Leu Ser Met Val
1               5                   10                  15

<210> SEQ ID NO 39
<211> LENGTH: 15
<212> TYPE: PRT
```

<400> SEQUENCE: 39

Gln Lys Arg Ile Leu Val Asn Leu Ser Met Val Glu Asn Lys Leu
1               5                   10                  15

<210> SEQ ID NO 40
<211> LENGTH: 15
<212> TYPE: PRT
<213> ORGANISM: Homo sapiens

<400> SEQUENCE: 40

Leu Val Asn Leu Ser Met Val Glu Asn Lys Leu Val Glu Leu Glu
1               5                   10                  15

<210> SEQ ID NO 41
<211> LENGTH: 15
<212> TYPE: PRT
<213> ORGANISM: Homo sapiens

<400> SEQUENCE: 41

Ser Met Val Glu Asn Lys Leu Val Glu Leu Glu His Thr Leu Leu
1               5                   10                  15

<210> SEQ ID NO 42
<211> LENGTH: 15
<212> TYPE: PRT
<213> ORGANISM: Homo sapiens

<400> SEQUENCE: 42

Asn Lys Leu Val Glu Leu Glu His Thr Leu Leu Ser Lys Gly Phe
1               5                   10                  15

<210> SEQ ID NO 43
<211> LENGTH: 15
<212> TYPE: PRT
<213> ORGANISM: Homo sapiens

<400> SEQUENCE: 43

Glu Leu Glu His Thr Leu Leu Ser Lys Gly Phe Arg Gly Ala Ser
1               5                   10                  15

<210> SEQ ID NO 44
<211> LENGTH: 15
<212> TYPE: PRT
<213> ORGANISM: Homo sapiens

<400> SEQUENCE: 44

Thr Leu Leu Ser Lys Gly Phe Arg Gly Ala Ser Pro His Arg Lys
1               5                   10                  15

<210> SEQ ID NO 45
<211> LENGTH: 15
<212> TYPE: PRT
<213> ORGANISM: Homo sapiens

<400> SEQUENCE: 45

Leu Ser Lys Gly Phe Arg Gly Ala Ser Pro His Arg Lys Ser Thr
1               5                   10                  15

<210> SEQ ID NO 46
<211> LENGTH: 8
<212> TYPE: PRT
<213> ORGANISM: Homo sapiens

<400> SEQUENCE: 46

Asn Thr Asp Asn Asn Leu Ala Val
1               5

<210> SEQ ID NO 47
<211> LENGTH: 11
<212> TYPE: PRT
<213> ORGANISM: Homo sapiens

<400> SEQUENCE: 47

Asn Ser Asn Thr Asp Asn Asn Leu Ala Val Tyr
1               5                   10

<210> SEQ ID NO 48
<211> LENGTH: 11
<212> TYPE: PRT
<213> ORGANISM: Homo sapiens

<400> SEQUENCE: 48

Asn Thr Asp Asn Asn Leu Ala Val Tyr Asp Leu
1               5                   10

<210> SEQ ID NO 49
<211> LENGTH: 10
<212> TYPE: PRT
<213> ORGANISM: Homo sapiens

<400> SEQUENCE: 49

Ser Asn Thr Asp Asn Asn Leu Ala Val Tyr
1               5                   10

<210> SEQ ID NO 50
<211> LENGTH: 9
<212> TYPE: PRT
<213> ORGANISM: Homo sapiens

<400> SEQUENCE: 50

Asn Ser Asn Thr Asp Asn Asn Leu Ala
1               5

<210> SEQ ID NO 51
<211> LENGTH: 10
<212> TYPE: PRT
<213> ORGANISM: Homo sapiens

<400> SEQUENCE: 51

Asn Ser Asn Thr Asp Asn Asn Leu Ala Val
1               5                   10

<210> SEQ ID NO 52
<211> LENGTH: 10
<212> TYPE: PRT
<213> ORGANISM: Homo sapiens

<400> SEQUENCE: 52

Asn Thr Asp Asn Asn Leu Ala Val Tyr Asp
1               5                   10

<210> SEQ ID NO 53
<211> LENGTH: 8
<212> TYPE: PRT
<213> ORGANISM: Homo sapiens

<400> SEQUENCE: 53

Thr Asp Asn Asn Leu Ala Val Tyr

<210> SEQ ID NO 54
<211> LENGTH: 8
<212> TYPE: PRT
<213> ORGANISM: Homo sapiens

<400> SEQUENCE: 54

Asn Ser Asn Thr Asp Asn Asn Leu
1               5

<210> SEQ ID NO 55
<211> LENGTH: 137
<212> TYPE: PRT
<213> ORGANISM: Mus musculus

<400> SEQUENCE: 55

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Thr
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Ser
            100                 105                 110

Val Met Gly Leu Arg Ile Leu Leu Leu Lys Val Ala Gly Phe Asn Leu
        115                 120                 125

Leu Met Thr Leu Arg Leu Trp Ser Ser
    130                 135

<210> SEQ ID NO 56
<211> LENGTH: 173
<212> TYPE: PRT
<213> ORGANISM: Mus musculus

<400> SEQUENCE: 56

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

```
Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170
```

<210> SEQ ID NO 57
<211> LENGTH: 137
<212> TYPE: PRT
<213> ORGANISM: Artificial Sequence
<220> FEATURE:
<223> OTHER INFORMATION: Synthetic

<400> SEQUENCE: 57

```
Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
                20                  25                  30

Asn Val Pro Lys Thr Met Glu Ser Gly Thr Phe Ile Thr Asp Lys Cys
            35                  40                  45

Val Leu Asp Met Lys Ala Met Asp Ser Lys Ser Asn Gly Ala Ile Ala
50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Leu
            100                 105                 110

Val Ile Val Leu Arg Ile Leu Leu Lys Val Ala Gly Phe Asn Leu
            115                 120                 125

Leu Met Thr Leu Arg Leu Trp Ser Ser
        130                 135
```

<210> SEQ ID NO 58
<211> LENGTH: 173
<212> TYPE: PRT
<213> ORGANISM: Artificial Sequence
<220> FEATURE:
<223> OTHER INFORMATION: Synthetic

<400> SEQUENCE: 58

```
Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
                20                  25                  30

Ala Arg Gly Phe Phe Pro Asp His Val Glu Leu Ser Trp Trp Val Asn
            35                  40                  45

Gly Lys Glu Val His Ser Gly Val Cys Thr Asp Pro Gln Ala Tyr Lys
50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
```

```
                115                 120                 125
Ile Thr Ser Ala Ser Tyr Gln Gln Gly Val Leu Ser Ala Thr Ile Leu
            130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

<210> SEQ ID NO 59
<211> LENGTH: 141
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Wherein X is any naturally occurring amino acid
      residue

<400> SEQUENCE: 59

Xaa Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
                20                  25                  30

Asn Val Ser Gln Ser Lys Asp Ser Asp Val Tyr Ile Thr Asp Lys Thr
            35                  40                  45

Val Leu Asp Met Arg Ser Met Asp Phe Lys Ser Asn Ser Ala Val Ala
        50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 60
<211> LENGTH: 177
<212> TYPE: PRT
<213> ORGANISM: Homo sapiens

<400> SEQUENCE: 60

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Phe Pro Asp His Val Glu Leu Ser Trp Trp Val Asn
            35                  40                  45

Gly Lys Glu Val His Ser Gly Val Ser Thr Asp Pro Gln Pro Leu Lys
        50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110
```

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 61
<211> LENGTH: 1800
<212> TYPE: DNA
<213> ORGANISM: Artificial Sequence
<220> FEATURE:
<223> OTHER INFORMATION: Synthetic

<400> SEQUENCE: 61

| | | | | | |
|---|---|---|---|---|---|
| atggcgaccc | gccttctctg | ttgggccgca | ctgtgtcttt | tgggcgctga | tcatactgga | 60 |
| gctgggtttt | cacagactcc | gtctaataaa | gtcactgaga | gggggaagta | cgtggaactc | 120 |
| cgctgtgatc | ccattagcgg | gcacactgca | ctctattggt | accggcagtc | tttgggacaa | 180 |
| ggacctgaat | tctgattta | cttccaggga | acgggggctg | ccgacgacag | tgggctgcca | 240 |
| aatgatcgat | tctttgcagt | taggcctgaa | ggtagcgtaa | gcacactgaa | gatacagagg | 300 |
| acagagagag | gggattcagc | agtctatctc | tgcgccagtt | cactgggaac | tggggggatac | 360 |
| aatgagcaat | tcttcgggcc | tggaacgcgc | ctcaccgtcc | tcgaggatct | ccggaacgtc | 420 |
| accccaccaa | aggtcagttt | gtttgagcca | tcaaaggcgg | agatcgccaa | caaacagaaa | 480 |
| gctacgctcg | tgtgtttggc | tcgggcttc | ttcccagacc | acgtagaact | tcctggtgg | 540 |
| gtcaatggaa | aggaggttca | ttccggagtg | tgcactgatc | cccaagcgta | caaggaatcc | 600 |
| aactatagct | actgtctctc | atctcggctc | cgggtgagtg | cgacattctg | cataatcct | 660 |
| cggaaccact | ttcgatgcca | agtgcagttt | catgggttga | gcgaggaaga | caagtggccc | 720 |
| gagggcagtc | ctaaaccagt | cactcaaaac | ataagcgccg | aggcatgggg | tagagccgat | 780 |
| tgtgggatta | ctagcgcttc | ataccaacaa | ggggtattga | gcgctacaat | tctttacgaa | 840 |
| attctcctcg | gcaaggcgac | gctctacgcc | gtactggtgt | ctactctcgt | ggttatggca | 900 |
| atggtgaaac | ggaaaaacag | cagagccaaa | agaagtggtt | ctggcgcgac | gaatttagt | 960 |
| ttgcttaagc | aagccggaga | tgtggaggaa | atcctggac | cgatgctgct | ggaacatctc | 1020 |
| ttgattatcc | tgtggatgca | actgacatgg | gtatcagggc | aacagcttaa | ccagagtccg | 1080 |
| cagtccatgt | tcattcagga | gggagaggat | gttagtatga | attgtacgag | ttcctccatc | 1140 |
| tttaatacgt | ggctctggta | taagcaagaa | ccaggagagg | gacctgtatt | gctgatagct | 1200 |
| ctttacaagg | caggagaact | gacaagcaac | ggtagattga | cagcacaatt | tgggattact | 1260 |
| aggaaggatt | cttccctcaa | tattagtgct | agcatcccat | cagatgtggg | gatctacttt | 1320 |
| tgtgcagggc | aactggttta | tgggaataaa | ctcgtctttg | gtgcgggaac | catcctgagg | 1380 |
| gtgaaaagta | atattcagaa | ccccgaacca | gccgtatatc | agttgaagga | cccaagatct | 1440 |
| caggatagta | cactctgttt | gtttacggac | tttgactcac | aaatcaacgt | cccgaagact | 1500 |
| atggaaagtg | gtacgttcat | cacagataag | tgcgttctgg | acatgaaggc | tatggactca | 1560 |
| aagagcaacg | gggcaattgc | cttggtccaac | cagacaagct | ttacctgtca | ggacattttt | 1620 |

-continued

```
aaggagacta atgctactta tccctccagc gacgttccgt gtgatgcgac tcttaccgag  1680
aagtcttttg agaccgatat gaatctcaac ttccagaatc tgctggttat tgtactgcgg  1740
atcctgcttc tgaaggttgc aggattcaat cttcttatga ctctccggct ctggtcttca  1800

<210> SEQ ID NO 62
<211> LENGTH: 179
<212> TYPE: PRT
<213> ORGANISM: Homo sapiens

<400> SEQUENCE: 62

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Tyr Pro Asp His Val Glu Leu Ser Trp Trp Val Asn
            35                  40                  45

Gly Lys Glu Val His Ser Gly Val Ser Thr Asp Pro Gln Pro Leu Lys
50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
            115                 120                 125

Ala Asp Cys Gly Phe Thr Ser Glu Ser Tyr Gln Gln Gly Val Leu Ser
130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly
```

ANTI-KK-LC-1 T CELL RECEPTORS

CROSS-REFERENCE TO RELATED APPLICATIONS

This patent application is the U.S. national stage of PCT/US2017/027865, filed Apr. 17, 2017, which claims the benefit of U.S. Provisional Patent Application No. 62/327,529, filed Apr. 26, 2016, each of which is incorporated by reference in its entirety herein.

STATEMENT REGARDING FEDERALLY SPONSORED RESEARCH AND DEVELOPMENT

This invention was made with Government support under project number ZIA BC 011478 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 39,613 Byte ASCII (Text) file named "740514_ST25.txt" dated Oct. 24, 2018.

BACKGROUND OF THE INVENTION

Adoptive cell therapy (ACT) involves the transfer of reactive T cells into patients, including the transfer of cancer-reactive T cells into cancer patients. ACT has been successful in mediating positive clinical outcomes in some cancer patients. However, obstacles to the widespread application of ACT remain. For example, one obstacle includes the difficulty in generating human T cells with anti-tumor potential. Another obstacle is that the transferred T cells can also be toxic to normal, i.e., non-cancerous tissues. Accordingly, there exists a need for improved immunological compositions and methods for treating cancer.

BRIEF SUMMARY OF THE INVENTION

An embodiment of the invention provides an isolated or purified T cell receptor (TCR) having antigenic specificity for Kita-Kyushu Lung Cancer Antigen $1_{52-60}$ (KK-LC-$1_{52-60}$).

Further embodiments of the invention provide related polypeptides, proteins, nucleic acids, recombinant expression vectors, host cells, populations of cells, and pharmaceutical compositions relating to the TCRs of the invention.

Further embodiments of the invention provide methods of detecting the presence of cancer in a mammal and methods of treating or preventing cancer in a mammal using the TCRs, polypeptides, proteins, nucleic acids, recombinant expression vectors, host cells, populations of cells, or pharmaceutical compositions of the invention.

DETAILED DESCRIPTION OF THE INVENTION

Figure 1A:
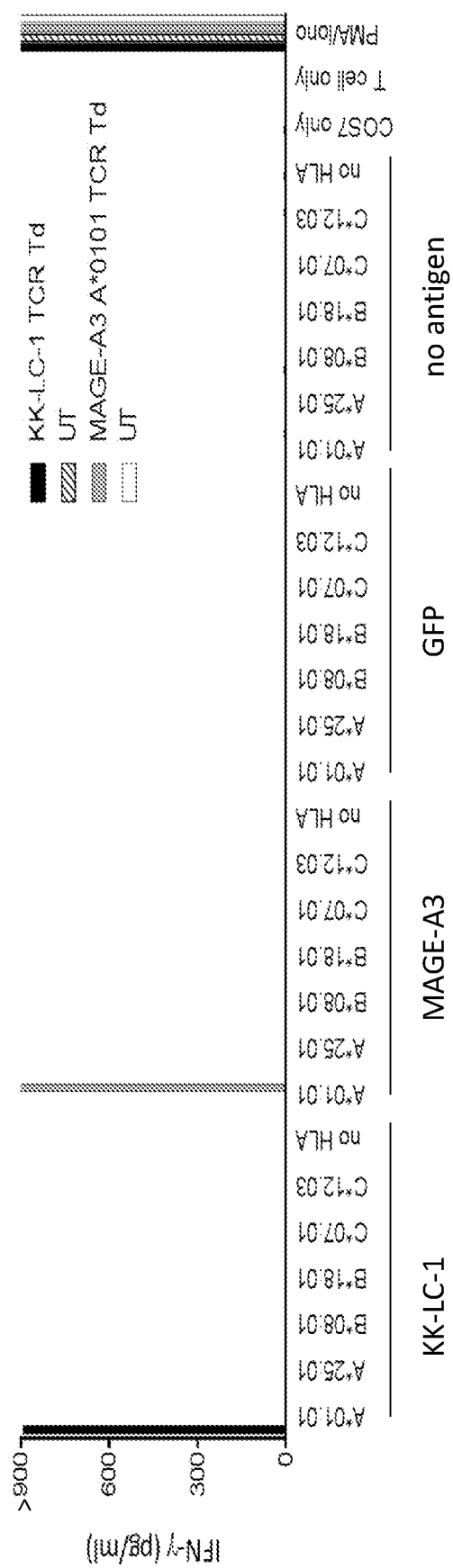
FIG. 1A is a graph showing the concentration of IFN-γ (pg/ml) secreted by untransduced (UT) effector cells (unshaded bars and horizontal striped bars), T cells transduced with a TCR targeting an HLA-A*01:01 restricted epitope of MAGE-A3$^{168-176}$ (grey bars), or T cells transduced with the vector of Example 2 encoding an anti-KK-LC-1 TCR (black bars) upon co-culture with COST cells (target cells) transfected with DNA encoding (i) no HLA molecule or one of patient 3853's six HLA-class I molecules (A*01:01, A*25:01, B*08:01, B*18:01, C*07:01, or C*12:03) and (ii) the KK-LC-1 antigen, control antigen MAGE-A3, control antigen GFP, or no antigen.

An embodiment of the invention provides an isolated or purified T cell receptor (TCR) having antigenic specificity for Kita-Kyushu Lung Cancer Antigen 1 (KK-LC-1) (also referred to as "CXorf61," "CT83," or "KKLC1"). KK-LC-1 belongs to a family of cancer antigens referred to as "cancer-testis antigens" (CTA) or cancer-germline antigens (CGA), which are expressed only in cancer cells and non-MHC expressing germ cells of the testis. KK-LC-1 is expressed in a variety of human cancers including, but not limited to, carcinomas of the bladder, uterine cervix, stomach, breast, lung, colon, rectum, and pancreas. The full-length KK-LC-1 protein may comprise, consist, or consist essentially of, SEQ ID NO: 1.

The inventive TCR may have antigenic specificity for any KK-LC-1 protein, polypeptide or peptide. In an embodiment of the invention, the TCR has antigenic specificity for a KK-LC-1 protein comprising, consisting of, or consisting essentially of, SEQ ID NO: 1. In a preferred embodiment of the invention, the TCR has antigenic specificity for a KK-LC-1$_{5260}$ peptide comprising, consisting of, or consisting essentially of, NTDNNLAVY (SEQ ID NO: 2).

In an embodiment of the invention, the inventive TCRs are able to recognize KK-LC-1 in a major histocompatibility complex (MHC) class I-dependent manner. "MHC class I-dependent manner," as used herein, means that the TCR elicits an immune response upon binding to KK-LC-1 within the context of an MHC class I molecule. The MHC class I molecule can be any MHC class I molecule known in the art, e.g., HLA-A molecules. In a preferred embodiment of the invention, the MHC class I molecule is an HLA-A1 molecule.

The TCRs of the invention may provide many advantages, including when expressed by cells used for adoptive cell transfer. Without being bound by a particular theory or mechanism, it is believed that because KK-LC-1 is expressed by cells of multiple cancer types, the inventive TCRs advantageously provide the ability to destroy cells of multiple types of cancer and, accordingly, treat or prevent multiple types of cancer. Additionally, without being bound to a particular theory or mechanism, it is believed that because KK-LC-1 is a CTA that is expressed only in tumor cells and non-MHC expressing germ cells of the testis (with low expression in the salivary gland and epididymis), the inventive TCRs advantageously target the destruction of cancer cells while minimizing or eliminating the destruction of normal, non-cancerous cells, thereby minimizing or eliminating toxicity. Because the salivary gland and epididymis are not essential for life, it is also believed that therapy with the inventive TCRs may reduce or avoid damage to tissues which are essential to life. Moreover, the inventive TCRs may, advantageously, successfully treat or prevent KK-LC-1-positive cancers that do not respond to other types of treatment such as, for example, chemotherapy alone, surgery, or radiation. Additionally, it is believed that the inventive TCRs may provide highly avid recognition of KK-LC-1, which may, advantageously, provide the ability to recognize unmanipulated tumor cells (e.g., tumor cells that have not been treated with interferon (IFN)-γ, transfected with a vector encoding one or both of KK-LC-1 and HLA-A1, pulsed with the KK-LC-1$_{52-60}$ peptide, or a combination thereof).

The phrase "antigenic specificity," as used herein, means that the TCR can specifically bind to and immunologically recognize KK-LC-1. For example, a TCR may be considered to have "antigenic specificity" for KK-LC-1 if T cells expressing the TCR secrete at least about 100 pg/mL or more (e.g., 200 pg/mL or more, 300 pg/mL or more, 400 pg/mL or more, 500 pg/mL or more, 600 pg/mL or more, 700 pg/mL or more, 1000 pg/mL or more, 5,000 pg/mL or more, 7,000 pg/mL or more, 10,000 pg/mL or more, or 20,000 pg/mL or more) of IFN-γ upon co-culture with antigen-negative HLA-A1$^+$ target cells pulsed with a low concentration of KK-LC-1 peptide (e.g., about 0.05 ng/mL to about 5 ng/mL, 0.05 ng/mL, 0.1 ng/mL, 0.5 ng/mL, 1 ng/mL, or 5 ng/mL). Alternatively or additionally, a TCR may be considered to have "antigenic specificity" for KK-LC-1 if T cells expressing the TCR secrete at least twice as much IFN-γ as the untransduced T cell background level of IFN-γ upon co-culture with antigen-negative HLA-A1$^+$ target cells pulsed with a low concentration of KK-LC-1 peptide. Cells expressing the inventive TCRs may also secrete IFN-γ upon co-culture with antigen-negative HLA-A1$^+$ target cells pulsed with higher concentrations of KK-LC-1 peptide.

An embodiment of the invention provides a TCR comprising two polypeptides (i.e., polypeptide chains), such as an alpha (α) chain of a TCR, a beta (β) chain of a TCR, a gamma (γ) chain of a TCR, a delta (δ) chain of a TCR, or a combination thereof. The polypeptides of the inventive TCR can comprise any amino acid sequence, provided that the TCR has antigenic specificity for KK-LC-1.

In an embodiment of the invention, the TCR comprises two polypeptide chains, each of which comprises a variable region comprising a complementarity determining region (CDR)1, a CDR2, and a CDR3 of a TCR. In an embodiment of the invention, the TCR comprises a first polypeptide chain comprising a CDR1 comprising the amino acid sequence of SEQ ID NO: 3 (CDR1 of α chain), a CDR2 comprising the amino acid sequence of SEQ ID NO: 4 (CDR2 of α chain), and a CDR3 comprising the amino acid sequence of SEQ ID NO: 5 (CDR3 of α chain), and a second polypeptide chain comprising a CDR1 comprising the amino acid sequence of SEQ ID NO: 6 (CDR1 of β chain), a CDR2 comprising the amino acid sequence of SEQ ID NO: 7 (CDR2 of β chain), and a CDR3 comprising the amino acid sequence of SEQ ID NO: 8 (CDR3 of β chain). In this regard, the inventive TCR can comprise any one or more of the amino acid sequences selected from the group consisting of SEQ ID NOs: 3-8. Preferably, the TCR comprises SEQ ID NOs: 3-5 or SEQ ID NOs: 6-8. In an especially preferred embodiment, the TCR comprises the amino acid sequences of SEQ ID NOs: 3-8.

In an embodiment of the invention, the TCR can comprise an amino acid sequence of a variable region of a TCR comprising the CDRs set forth above. In this regard, the TCR can comprise the amino acid sequence of SEQ ID NO: 9 (the variable region of a human α chain); SEQ ID NO: 10, wherein X at position 2 of SEQ ID NO: 10 is Ala or Gly (the variable region of a β chain); both SEQ ID NOs: 9 and 10, wherein X at position 2 of SEQ ID NO: 10 is Ala or Gly; SEQ ID NO: 11 (the variable region of a human β chain); or both SEQ ID NOs: 9 and 11. SEQ ID NO: 10 corresponds to SEQ ID NO: 11 when X at position 2 of SEQ ID NO: 10 is Gly. Preferably, the inventive TCR comprises the amino acid sequences of both SEQ ID NOs: 9 and 10, wherein X at position 2 of SEQ ID NO: 10 is Ala.

The inventive TCRs may further comprise a constant region derived from any suitable species such as, e.g., human or mouse. As used herein, the term "murine" or "human," when referring to a TCR or any component of a TCR described herein (e.g., complementarity determining region (CDR), variable region, constant region, alpha chain, and/or beta chain), means a TCR (or component thereof) which is derived from a mouse or a human, respectively, i.e., a TCR (or component thereof) that originated from or was, at one time, expressed by a mouse T cell or a human T cell, respectively.

In an embodiment of the invention, the TCRs further comprise a human constant region. In this regard, the TCR can comprise the amino acid sequence of SEQ ID NO: 59, wherein X at position 1 is any naturally occurring amino acid residue (the constant region of a human α chain), SEQ ID NO: 60 (the constant region of a human β chain), SEQ ID NO: 62 (the constant region of a human β chain), both SEQ ID NOs: 59 and 62, or both SEQ ID NOs: 59 and 60.

In an embodiment of the invention, the TCR comprises a murine constant region. For example, the TCR may be a chimeric TCR comprising a human variable region and a murine constant region. In this regard, the TCR can comprise SEQ ID NO: 55 (constant region of a murine α chain); SEQ ID NO: 56 (constant region of a murine β chain); or both SEQ ID NO: 55 and SEQ ID NO: 56. The chimeric TCR may comprise any of the CDR regions as described herein with respect to other aspects of the invention. In another embodiment of the invention, the chimeric TCR may comprise any of the variable regions described herein with respect to other aspects of the invention. In an embodiment of the invention, the TCR comprises a murine constant region, optionally with one, two, three, or four amino acid substitution(s) in the constant region of one or both of the alpha and beta chains, as described herein with respect to other aspects of the invention. In an embodiment of the invention, the TCR comprises a murine constant region, optionally with one, two, three, or four amino acid substitution(s) in the murine constant region of the alpha chain and one amino acid substitution in the murine constant region of the beta chain, as described herein with respect to other aspects of the invention.

In an embodiment of the invention, the inventive TCR may comprise a combination of a variable region and a constant region. In this regard, the TCR can comprise an alpha chain comprising the amino acid sequences of both of SEQ ID NO: 9 (the variable region of a human α chain) and SEQ ID NO: 59 (the constant region of a human α chain); a beta chain comprising the amino acid sequences of both of SEQ ID NO: 11 (the variable region of a human β chain) and SEQ ID NO: 60 (the constant region of a human β chain); a beta chain comprising the amino acid sequences of both of SEQ ID NO: 11 (the variable region of a human β chain) and SEQ ID NO: 62 (the constant region of a human β chain); a beta chain comprising the amino acid sequences of both of SEQ ID NO: 10, wherein X at position 2 of SEQ ID NO: 2 is Ala or Gly (the variable region of a β chain) and SEQ ID NO: 60 (the constant region of a human β chain); a beta chain comprising the amino acid sequences of both of SEQ ID NO: 10 (the variable region of a human β chain) and SEQ ID NO: 62 (the constant region of a human β chain); the amino acid sequences of all of SEQ ID NOs: 9, 11, 59, and 60; the amino acid sequences of all of SEQ ID NOs: 9, 10, 59, and 60; the amino acid sequences of all of SEQ ID NOs: 9, 11, 59, and 62; or the amino acid sequences of all of SEQ ID NOs: 9, 10, 59, and 62.

In an embodiment of the invention, the inventive TCR may comprise an alpha chain comprising the amino acid sequences of both of SEQ ID NO: 9 (the variable region of a human α chain) and SEQ ID NO: 55 (the constant region of a murine α chain); a beta chain comprising the amino acid sequences of both of SEQ ID NO: 11 (the variable region of a human β chain) and SEQ ID NO: 56 (the constant region of a murine β chain); a beta chain comprising the amino acid sequences of both of SEQ ID NO: 10, wherein X at position 2 of SEQ ID NO: 2 is Ala or Gly (the variable region of a β chain) and SEQ ID NO: 56 (the constant region of a murine β chain); the amino acid sequences of all of SEQ ID NOs: 9, 11, 55, and 56; or the amino acid sequences of all of SEQ ID NOs: 9, 10, 55, and 56.

In an embodiment of the invention, the TCR comprises the amino acid sequence of any of the TCRs described herein with one, two, three, or four amino acid substitution (s) in the constant region of one or both of the alpha and beta chains. Preferably, the TCR comprises a murine constant region with one, two, three, or four amino acid substitution (s) in the murine constant region of one or both of the alpha and beta chains. In an especially preferred embodiment, the TCR comprises a murine constant region with one, two, three, or four amino acid substitution(s) in the murine constant region of the alpha chain and one amino acid substitution in the murine constant region of the beta chain. In some embodiments, the TCRs comprising the substituted amino acid sequence(s) advantageously provide one or more of increased recognition of KK-LC-1$^+$ targets, increased expression by a host cell, and increased anti-tumor activity as compared to the parent TCR comprising an unsubstituted amino acid sequence. In general, the substituted amino acid sequences of the murine constant regions of the TCR α and β chains, SEQ ID NOs: 13 and 14, respectively, correspond with all or portions of the unsubstituted murine constant region amino acid sequences SEQ ID NOs: 55 and 56, respectively, with SEQ ID NO: 13 having one, two, three, or four amino acid substitution(s) when compared to SEQ ID NO: 55 and SEQ ID NO: 14 having one amino acid substitution when compared to SEQ ID NO: 56. In this regard, an embodiment of the invention provides a TCR comprising the amino acid sequences of one or both of (a) SEQ ID NO: 13 (constant region of alpha chain), wherein (i) X at position 48 is Thr or Cys; (ii) X at position 112 is Ser, Gly, Ala, Val, Leu, Ile, Pro, Phe, Met, or Trp; (iii) X at position 114 is Met, Gly, Ala, Val, Leu, Ile, Pro, Phe, Met, or Trp; and (iv) X at position 115 is Gly, Ala, Val, Leu, Ile, Pro, Phe, Met, or Trp; and (b) SEQ ID NO: 14 (constant region of beta chain), wherein X at position 57 is Ser or Cys. In an embodiment of the invention, the TCR comprising SEQ ID NO: 13 does not comprise SEQ ID NO: 55 (unsubstituted murine constant region of alpha chain). In an embodiment of the invention, the TCR comprising SEQ ID NO: 14 does not comprise SEQ ID NO: 56 (unsubstituted murine constant region of beta chain).

In an embodiment of the invention, the substituted amino acid sequence includes cysteine substitutions in the constant region of one or both of the α and β chains to provide a cysteine-substituted TCR. Opposing cysteines in the α and the β chains provide a disulfide bond that links the constant regions of the α and the β chains of the substituted TCR to one another and which is not present in a TCR comprising the unsubstituted human constant region or the unsubstituted murine constant region. In this regard, the TCR is a cysteine-substituted TCR in which one or both of the native Thr48 of SEQ ID NO: 55 and the native Ser57 of SEQ ID NO: 56 may be substituted with Cys. Preferably, both of the native Thr48 of SEQ ID NO: 55 and the native Ser57 of SEQ ID NO: 56 are substituted with Cys. In an embodiment, the cysteine-substituted TCR comprises an alpha chain constant region comprising the amino acid sequence of SEQ ID NO: 13, wherein X at position 48 is Cys, X at position 112 is the native Ser, X at position 114 is the native Met, and X at position 115 is the native Gly, and a beta chain constant region comprising the amino acid sequence of SEQ ID NO: 14, wherein X at position 57 is Cys. The cysteine-substituted TCRs of the invention may include the substituted constant region in addition to any of the CDRs or variable regions described herein.

In an embodiment of the invention, the substituted amino acid sequence includes substitutions of one, two, or three amino acids in the transmembrane (TM) domain of the constant region of one or both of the α and β chains with a hydrophobic amino acid to provide a hydrophobic amino acid-substituted TCR. The hydrophobic amino acid substitution(s) in the TM domain of the TCR may increase the hydrophobicity of the TM domain of the TCR as compared to a TCR that lacks the hydrophobic amino acid substitution(s) in the TM domain. In this regard, the TCR may be a hydrophobic amino acid-substituted TCR in which one, two, or three of the native Ser112, Met114, and Gly115 of SEQ ID NO: 55 may, independently, be substituted with Gly, Ala, Val, Leu, Ile, Pro, Phe, Met, or Trp; preferably with Leu, Ile, or Val. Preferably, all three of the native Ser112, Met114, and Gly115 of SEQ ID NO: 55 are, independently, substituted with Gly, Ala, Val, Leu, Ile, Pro, Phe, Met, or Trp; preferably with Leu, Ile, or Val. In an embodiment, the hydrophobic amino acid-substituted TCR comprises an alpha chain constant region comprising the amino acid sequence of SEQ ID NO: 13, wherein X at position 48 is the native Thr, X at position 112 is Ser, Gly, Ala, Val, Leu, Ile, Pro, Phe, Met, or Trp, X at position 114 is Met, Gly, Ala, Val, Leu, Ile, Pro, Phe, Met, or Trp, and X at position 115 is Gly, Ala, Val, Leu, Ile, Pro, Phe, Met, or Trp, and a beta chain constant region comprising the amino acid sequence of SEQ ID NO: 14, wherein X at position 57 is the native Ser, wherein the hydrophobic amino acid-substituted TCR comprising SEQ ID NO: 13 does not comprise SEQ ID NO: 55 (unsubstituted murine constant region of alpha chain). Preferably, the hydrophobic amino acid-substituted TCR comprises an alpha chain constant region comprising the amino acid sequence of SEQ ID NO: 13, wherein X at position 48 is the native Thr, X at position 112 is Leu, X at position 114 is Ile, and X at position 115 is Val, and a beta chain constant region comprising the amino acid sequence of SEQ ID NO: 14, wherein X at position 57 is the native Ser. The hydrophobic amino acid-substituted TCRs of the invention may include the substituted constant region in addition to any of the CDRs or variable regions described herein.

In an embodiment of the invention, the substituted amino acid sequence includes the cysteine substitutions in the constant region of one or both of the α and β chains in combination with the substitution(s) of one, two, or three amino acids in the transmembrane (TM) domain of the constant region of one or both of the α and β chains with a hydrophobic amino acid (also referred to herein as "cysteine-substituted, hydrophobic amino acid-substituted TCR"). In this regard, the TCR is a cysteine-substituted, hydrophobic amino acid-substituted TCR in which the native Thr48 of SEQ ID NO: 55 is substituted with Cys; one, two, or three of the native Ser112, Met114, and Gly115 of SEQ ID NO: 55 are, independently, substituted with Gly, Ala, Val, Leu, Ile, Pro, Phe, Met, or Trp; preferably with Leu, Ile, or Val; and the native Ser57 of SEQ ID NO: 56 is substituted with Cys. Preferably, all three of the native Ser112, Met114, and Gly115 of SEQ ID NO: 55 are, independently, substituted with Gly, Ala, Val, Leu, Ile, Pro, Phe, Met, or Trp; preferably with Leu, Ile, or Val. In an embodiment, the cysteine-substituted, hydrophobic amino acid-substituted TCR comprises an alpha chain constant region comprising the amino acid sequence of SEQ ID NO: 13, wherein X at position 48 is Cys, X at position 112 is Ser, Gly, Ala, Val, Leu, Ile, Pro, Phe, Met, or Trp, X at position 114 is Met, Gly, Ala, Val, Leu, Ile, Pro, Phe, Met, or Trp, and X at position 115 is Gly, Ala, Val, Leu, Ile, Pro, Phe, Met, or Trp, and a beta chain constant region comprising the amino acid sequence of SEQ ID NO: 14, wherein X at position 56 is Cys, wherein the cysteine-substituted, hydrophobic amino acid-substituted TCR comprising SEQ ID NO: 13 does not comprise SEQ ID NO: 55 (unsubstituted murine constant region of alpha chain). Preferably, the cysteine-substituted, hydrophobic amino acid-substituted TCR comprises an alpha chain constant region comprising the amino acid sequence of SEQ ID NO: 57 and a beta chain constant region comprising the amino acid sequence of SEQ ID NO: 58. The cysteine-substituted, hydrophobic amino acid-substituted, TCRs of the invention may include the substituted constant region in addition to any of the CDRs or variable regions described herein. In this regard, the cysteine-substituted, hydrophobic amino acid-substituted TCR can comprise (i) SEQ ID NOs: 3-5 and 57; (ii) SEQ ID NO: 9 and 57; (iii) SEQ ID NOs: 6-8 and 58; (iv) SEQ ID NO: 10 and 58, wherein X at position 2 of SEQ ID NO: 10 is Ala or Gly; or (v) SEQ ID NO: 11 and 58. Preferably, the cysteine-substituted, hydrophobic amino acid-substituted TCR comprises the amino acid sequences of (i) SEQ ID NOs: 3-8 and 57 and 58; (ii) SEQ ID NOs: 9-10 and 57 and 58; or (iii) SEQ ID NOs: 9, 11, and 57 and 58. In an especially preferred embodiment, the cysteine-substituted, hydrophobic amino acid-substituted TCR comprises a full-length alpha chain comprising the amino acid sequence of SEQ ID NO: 15 and a full-length beta chain comprising the amino acid sequence of SEQ ID NO: 16. In this regard, the Cys-substituted, hydrophobic amino acid-substituted TCR can comprise SEQ ID NO: 15, SEQ ID NO: 16, or both SEQ ID NOs: 15 and 16.

Also provided by the invention is a polypeptide comprising a functional portion of any of the TCRs described herein. The term "polypeptide" as used herein includes oligopeptides and refers to a single chain of amino acids connected by one or more peptide bonds.

With respect to the inventive polypeptides, the functional portion can be any portion comprising contiguous amino acids of the TCR of which it is a part, provided that the functional portion specifically binds to KK-LC-1. The term "functional portion," when used in reference to a TCR, refers to any part or fragment of the TCR of the invention, which part or fragment retains the biological activity of the TCR of which it is a part (the parent TCR). Functional portions encompass, for example, those parts of a TCR that retain the ability to specifically bind to KK-LC-1 (e.g., in an HLA-A1-dependent manner), or detect, treat, or prevent cancer, to a similar extent, the same extent, or to a higher extent, as the parent TCR. In reference to the parent TCR, the functional portion can comprise, for instance, about 10%, 25%, 30%, 50%, 68%, 80%, 90%, 95%, or more, of the parent TCR.

The functional portion can comprise additional amino acids at the amino or carboxy terminus of the portion, or at both termini, which additional amino acids are not found in the amino acid sequence of the parent TCR. Desirably, the additional amino acids do not interfere with the biological function of the functional portion, e.g., specifically binding to KK-LC-1; and/or having the ability to detect cancer, treat or prevent cancer, etc. More desirably, the additional amino acids enhance the biological activity, as compared to the biological activity of the parent TCR.

The polypeptide can comprise a functional portion of either or both of the α and β chains of the TCRs of the invention, such as a functional portion comprising one of more of CDR1, CDR2, and CDR3 of the variable region(s) of the α chain and/or β chain of a TCR of the invention. In an embodiment of the invention, the polypeptide can comprise a functional portion comprising the amino acid sequence of SEQ ID NO: 3 (CDR1 of α chain), 4 (CDR2 of α chain), 5 (CDR3 of α chain), 6 (CDR1 of β chain), 7 (CDR2 of β chain), 8 (CDR3 of β chain), or a combination thereof. Preferably, the inventive polypeptide comprises the amino acid sequences of SEQ ID NOs: 3-5; 6-8; or all of SEQ ID NOs: 3-8. More preferably, the polypeptide comprises the amino acid sequences of all of SEQ ID NOs: 3-8.

In an embodiment of the invention, the inventive polypeptide can comprise, for instance, the variable region of the inventive TCR comprising a combination of the CDR regions set forth above. In this regard, the polypeptide can comprise the amino acid sequence of SEQ ID NO: 9 (the variable region of an α chain), SEQ ID NO: 10, wherein X at position 2 of SEQ ID NO: 10 is Ala or Gly (the variable region of a β chain), SEQ ID NO: 11 (the variable region of a β chain), both SEQ ID NOs: 9 and 10, or both SEQ ID NOs: 9 and 11. Preferably, the polypeptide comprises the amino acid sequences of both SEQ ID NOs: 9 and 10, wherein X at position 2 of SEQ ID NO: 10 is Ala.

The inventive polypeptide may further comprise a constant region derived from any suitable species such as, e.g., human or mouse, described herein or any of the substituted constant regions described herein. In this regard, the polypeptide can comprise the amino acid sequence of SEQ ID NO: 59 (the constant region of a human α chain), SEQ ID NO: 60 (the constant region of a human β chain), SEQ ID NO: 62 (the constant region of a human β chain), SEQ ID NO: 13 (constant region of α chain, substituted as described herein with respect to other aspects of the invention), SEQ ID NO: 55 (the unsubstituted constant region of a murine α chain), SEQ ID NO: 14 (constant region of β chain, substituted as described herein with respect to other aspects of the invention), SEQ ID NO: 56 (the unsubstituted constant region of a murine β chain), SEQ ID NO: 57 (constant region of a cysteine-substituted, hydrophobic amino acid-substituted α chain), SEQ ID NO: 58 (constant region of a cysteine-substituted, hydrophobic amino acid-substituted β chain), both SEQ ID NOs: 13 and 14, both SEQ ID NOs: 55 and 56, or both SEQ ID NOs: 57 and 58.

In an embodiment of the invention, the inventive polypeptide may comprise a combination of a variable region and a constant region. In this regard, the polypeptide can comprise both SEQ ID NOs: 9 and 13, both SEQ ID NOs: 9 and 55, both SEQ ID NOs: 9 and 57, both SEQ ID NOs: 10 and 14, both SEQ ID NOs: 10 and 56, both SEQ ID NOs: 10 and 58, both SEQ ID NOs: 11 and 14, both SEQ ID NOs: 11 and 56, both SEQ ID NOs: 11 and 58, all of SEQ ID NOs: 3-5 and 13, all of SEQ ID NOs: 3-5 and 55, all of SEQ ID NOs: 3-5 and 57, all of SEQ ID NOs: 6-8 and 14, all of SEQ ID NOs: 6-8 and 56, all of SEQ ID NOs: 6-8 and 58, all of SEQ ID NOs: 3-8 and 13-14, all of SEQ ID NOs: 3-8 and 55 and 56, or all of SEQ ID NOs: 3-8 and 57 and 58. SEQ ID NOs: 13 and 14 may be substituted as described herein with respect to other aspects of the invention.

In an embodiment of the invention, the inventive polypeptide can comprise the entire length of an α or β chain of one of the TCRs described herein. In this regard, the inventive polypeptide can comprise an amino acid sequence of one or both of SEQ ID NO: 15 and 16. Preferably, the polypeptide comprises SEQ ID NO: 15 and SEQ ID NO: 16.

The invention further provides a protein comprising at least one of the polypeptides described herein. By "protein" is meant a molecule comprising one or more polypeptide chains.

In an embodiment, the protein of the invention can comprise a first polypeptide chain comprising the amino acid sequences of SEQ ID NOs: 3-5 and a second polypeptide chain comprising the amino acid sequence of SEQ ID NOs: 6-8. Alternatively or additionally, the protein of the invention can comprise (i) a first polypeptide chain comprising the amino acid sequence of SEQ ID NO: 9 and a second polypeptide chain comprising the amino acid sequence of SEQ ID NO: 10, wherein (i) X at position 2 of SEQ ID NO: 10 is Ala or Gly; (ii) a first polypeptide chain comprising the amino acid sequence of SEQ ID NO: 9 and a second polypeptide chain comprising the amino acid sequence of SEQ ID NO: 11; or (iii) a first polypeptide chain comprising the amino acid sequence of SEQ ID NO: 13 and a second polypeptide chain comprising the amino acid sequence of SEQ ID NO: 14. SEQ ID NOs: 13 and 14 may be substituted as described herein with respect to other aspects of the invention. The protein can, for example, comprise a first polypeptide chain comprising the amino acid sequence of SEQ ID NO: 15 and a second polypeptide chain comprising the amino acid sequence of SEQ ID NO: 16. In this instance, the protein of the invention can be a TCR. Alternatively, if, for example, the protein comprises a single polypeptide chain comprising SEQ ID NO: 15 and 16, all of SEQ ID NOs: 3-8 and 13 and 14; all of SEQ ID NOs:

3-8 and 55 and 56, all of SEQ ID NOs: 3-8 and 57 and 58; all of SEQ ID NOs: 9, 10, 13, and 14; all of SEQ ID NOs: 9, 11, 13, and 14; all of SEQ ID NOs: 9, 10, 55, and 56; all of SEQ ID NO: 9, 10, 57, and 58; or all of SEQ ID NOs: 9, 11, 57, and 58, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods.

In some embodiments of the invention, the TCRs, polypeptides, and proteins of the invention may be expressed as a single protein comprising a linker peptide linking the α chain and the β chain. In this regard, the TCRs, polypeptides, and proteins of the invention may further comprise a linker peptide. The linker peptide may advantageously facilitate the expression of a recombinant TCR, polypeptide, and/or protein in a host cell. The linker peptide may comprise any suitable amino acid sequence. In an embodiment of the invention, the linker is a furin/Ser/Gly/P2A linker. For example, the linker peptide may comprise SEQ ID NO: 17. In an embodiment of the invention, the protein comprising an alpha chain, beta chain, and a linker may comprise the amino acid sequence of SEQ ID NO: 12 (cysteine substituted, hydrophobic amino acid-substituted TCR full-length alpha and beta chains joined by a linker). Upon expression of the construct including the linker peptide by a host cell, the linker peptide may be cleaved, resulting in separated α and β chains.

The protein of the invention can be a recombinant antibody comprising at least one of the inventive polypeptides described herein. As used herein, "recombinant antibody" refers to a recombinant (e.g., genetically engineered) protein comprising at least one of the polypeptides of the invention and a polypeptide chain of an antibody, or a portion thereof. The polypeptide of an antibody, or portion thereof, can be a heavy chain, a light chain, a variable or constant region of a heavy or light chain, a single chain variable fragment (scFv), or an Fc, Fab, or F(ab)$_2$' fragment of an antibody, etc. The polypeptide chain of an antibody, or portion thereof, can exist as a separate polypeptide of the recombinant antibody. Alternatively, the polypeptide chain of an antibody, or portion thereof, can exist as a polypeptide, which is expressed in frame (in tandem) with the polypeptide of the invention. The polypeptide of an antibody, or portion thereof, can be a polypeptide of any antibody or any antibody fragment.

The TCRs, polypeptides, and proteins of the invention can be of any length, i.e., can comprise any number of amino acids, provided that the TCRs, polypeptides, or proteins retain their biological activity, e.g., the ability to specifically bind to KK-LC-1; detect cancer; or treat or prevent cancer in a mammal, etc. For example, the polypeptide can be in the range of from about 50 to about 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The TCRs, polypeptides, and proteins of the invention of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The TCRs, polypeptides, and proteins of the invention can be glycosylated, amidated, carboxylated, phosphorylated, esterified, N-acylated, cyclized via, e.g., a disulfide bridge, or converted into an acid addition salt and/or optionally dimerized or polymerized, or conjugated.

Included in the scope of the invention are functional variants of the inventive TCRs, polypeptides, and proteins described herein. The term "functional variant," as used herein, refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to KK-LC-1 for which the parent TCR has antigenic specificity or to which the parent polypeptide or protein specifically binds, to a similar extent, the same extent, or to a higher extent, as the parent TCR, polypeptide, or protein. In reference to the parent TCR, polypeptide, or protein, the functional variant can, for instance, be at least about 30%, 50%, 75%, 80%, 90%, 95%, 96%, 97%, 98%, 99% or more identical in amino acid sequence to the parent TCR, polypeptide, or protein.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

The TCR, polypeptide, or protein can consist essentially of the specified amino acid sequence or sequences described herein, such that other components of the TCR, polypeptide, or protein, e.g., other amino acids, do not materially change the biological activity of the TCR, polypeptide, or protein. In this regard, the inventive TCR, polypeptide, or protein can, for example, consist essentially of the amino acid sequence of any one or both of SEQ ID NOs: 15 and 16. Also, for instance, the inventive TCRs, polypeptides, or proteins can consist essentially of the amino acid sequence(s) of SEQ ID NO: 9, 10, 11, both SEQ ID NOs: 9 and 10, or both SEQ ID NOs: 9 and 11. Furthermore, the inventive TCRs, polypeptides, or proteins can consist essentially of the amino acid sequence of SEQ ID NO: 3 (CDR1 of α chain), SEQ ID NO: 4 (CDR2 of α chain), SEQ ID NO: 5 (CDR3 of α chain), SEQ ID NO: 6 (CDR1 of β chain), SEQ ID NO: 7 (CDR2 of β chain), SEQ ID NO: 8 (CDR3 of β chain), or any combination thereof, e.g., SEQ ID NOs: 3-5; 6-8; or 3-8.

The TCR, polypeptide, and/or protein of the invention can be obtained by methods known in the art. Suitable methods of de novo synthesizing polypeptides and proteins are known in the art. Also, polypeptides and proteins can be recombinantly produced using the nucleic acids described herein using standard recombinant methods. See, for instance, Green and Sambrook, *Molecular Cloning: A Laboratory Manual*, 4$^{th}$ ed., Cold Spring Harbor Press, Cold Spring Harbor, N.Y. 2012. Further, some of the TCRs, polypeptides, and proteins of the invention can be isolated and/or purified from a source, such as a plant, a bacterium, an insect, a mammal, e.g., a rat, a human, etc. Methods of isolation and purification are well-known in the art. Alternatively, the TCRs, polypeptides, and/or proteins described herein can be commercially synthesized by companies, such as Synpep (Dublin, Calif.), Peptide Technologies Corp. (Gaithersburg, Md.), and Multiple Peptide Systems (San Diego, Calif.). In this respect, the inventive TCRs, polypeptides, and proteins can be synthetic, recombinant, isolated, and/or purified.

Included in the scope of the invention are conjugates, e.g., bioconjugates, comprising any of the inventive TCRs, polypeptides, or proteins, nucleic acids, recombinant expression vectors, host cells, or populations of host cells. Conjugates, as well as methods of synthesizing conjugates in general, are known in the art.

An embodiment of the invention provides a nucleic acid sequence comprising a nucleotide sequence encoding any of the TCRs, polypeptides, or proteins described herein. "Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In an embodiment, the nucleic acid comprises complementary DNA (cDNA). It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Green and Sambrook et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N$^6$-isopentenyladenine, 1-methylguanine, 1-methylinosine, 2,2-dimethylguanine, 2-methyladenine, 2-methylguanine, 3-methylcytosine, 5-methylcytosine, N$^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N$^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any nucleotide sequence which encodes any of the TCRs, polypeptides, or proteins described herein. In an embodiment of the invention, the nucleotide sequence may comprise, consist, or consist essentially of SEQ ID NO: 61. The nucleotide sequence of SEQ ID NO: 61 encodes the amino acid sequence of SEQ ID NO: 12 (cysteine substituted, hydrophobic amino acid-substituted TCR full-length alpha and beta chains joined by a linker).

In an embodiment of the invention, the nucleic acid comprises a codon-optimized nucleotide sequence. Without being bound to a particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency. For example, the nucleotide sequence of SEQ ID NO: 61 is codon-optimized for expression in a human cell.

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs. It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

The nucleic acids of the invention can be incorporated into a recombinant expression vector. In this regard, the invention provides recombinant expression vectors comprising any of the nucleic acids of the invention. In an embodiment of the invention, the recombinant expression vector comprises a nucleotide sequence encoding the α chain, the β chain, and linker peptide. For example, in an embodiment, the recombinant expression vector comprises a nucleotide sequence encoding the full-length alpha and beta chains of the inventive TCR with a linker positioned between them, wherein the nucleotide sequence encoding the beta chain is positioned 5' of the nucleotide sequence encoding the alpha chain. In an embodiment of the invention, the nucleotide sequence encodes the full-length alpha and beta chains of the inventive TCR with a linker positioned between them, wherein the nucleotide sequence encoding the beta chain is positioned 3' of the nucleotide sequence encoding the alpha chain.

For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do not hinder the transcription or replication of the vector.

The recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector. In an especially preferred embodiment, the recombinant expression vector is an MSGV1 vector.

In a preferred embodiment, the recombinant expression vector comprises a nucleotide sequence encoding an alpha chain and a beta chain of any of the TCRs described herein, wherein the nucleotide sequence encoding the beta chain is positioned 5' of the nucleotide sequence encoding the alpha chain. In this regard, the nucleotide sequence encoding the alpha chain may be positioned 3' of the nucleotide sequence encoding the beta chain. Without being bound by a particular theory or mechanism, it is believed that a nucleotide sequence encoding a beta chain that is positioned 5' of the nucleotide sequence encoding the alpha chain may provide any one or more of increased recognition of KK-LC-1+ targets, increased expression by a host cell, and increased anti-tumor activity as compared to a nucleotide sequence encoding a beta chain that is positioned 3' of the nucleotide sequence encoding the alpha chain. In a less preferred embodiment, the nucleotide sequence encoding the beta chain is positioned 3' of the nucleotide sequence encoding the alpha chain. In this regard, the nucleotide sequence encoding the alpha chain may be positioned 5' of the nucleotide sequence encoding the beta chain.

The recombinant expression vectors of the invention can be prepared using standard recombinant DNA techniques described in, for example, Green and Sambrook et al. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papillomavirus, and the like.

Desirably, the recombinant expression vector comprises regulatory sequences, such as transcription and translation initiation and termination codons, which are specific to the type of host cell (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected host cells. Marker genes include biocide resistance, e.g., resistance to antibiotics, heavy metals, etc., complementation in an auxotrophic host cell to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the TCR, polypeptide, or protein, or to the nucleotide sequence which is complementary to or which hybridizes to the nucleotide sequence encoding the TCR, polypeptide, or protein. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression. Further, the recombinant expression vectors can be made to include a suicide gene.

As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine daminase, purine nucleoside phosphorylase, and nitroreductase.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α $E.$ $coli$ cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL) or a peripheral blood mononuclear cell (PBMC). More preferably, the host cell is a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, $CD4^+$/$CD8^+$ double positive T cells, $CD4^+$ helper T cells, e.g., $Th_1$ and $Th_2$ cells, $CD4^+$ T cells, $CD8^+$ T cells (e.g., cytotoxic T cells), tumor infiltrating lymphocytes (TILs), memory T cells (e.g., central memory T cells and effector memory T cells), naïve T cells, and the like.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

In an embodiment of the invention, the numbers of cells in the population may be rapidly expanded. Expansion of the numbers of T cells can be accomplished by any of a number of methods as are known in the art as described in, for example, U.S. Pat. Nos. 8,034,334; 8,383,099; U.S. Patent Application Publication No. 2012/0244133; Dudley et al., *J. Immunother.*, 26:332-42 (2003); and Riddell et al., *J. Immunol. Methods,* 128:189-201 (1990). For example, expansion of the numbers of T cells may be carried out by culturing the T cells with OKT3 antibody, IL-2, and feeder PBMC (e.g., irradiated allogeneic PBMC).

The inventive TCRs, polypeptides, proteins, nucleic acids, recombinant expression vectors, and host cells (including populations thereof) can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70%, 80%, 90%, 95%, or can be 100%.

The inventive TCRs, polypeptides, proteins, nucleic acids, recombinant expression vectors, and host cells (including populations thereof), all of which are collectively referred to as "inventive TCR materials" hereinafter, can be formulated into a composition, such as a pharmaceutical composition. In this regard, the invention provides a pharmaceutical composition comprising any of the TCRs, polypeptides, proteins, nucleic acids, expression vectors, and host cells (including populations thereof) described herein, and a pharmaceutically acceptable carrier. The inventive pharmaceutical compositions containing any of the inventive TCR materials can comprise more than one inventive TCR material, e.g., a polypeptide and a nucleic acid, or two or more different TCRs. Alternatively, the pharmaceutical composition can comprise an inventive TCR material in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR material under consideration. Such pharmaceutically acceptable carriers are well-known to those skilled in the art and are readily available to the public. It is preferred that the pharmaceutically acceptable carrier be one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. Suitable formulations may include any of those for oral, parenteral, subcutaneous, intratumoral, intravenous, intramuscular, intraarterial, intrathecal, or interperitoneal administration. More than one route can be used to administer the inventive TCR materials, and in certain instances, a particular route can provide a more immediate and more effective response than another route.

Preferably, the inventive TCR material is administered by injection, e.g., intravenously. When the inventive TCR material is a host cell expressing the inventive TCR, the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumen.

For purposes of the invention, the amount or dose (e.g., numbers of cells when the inventive TCR material is one or more cells) of the inventive TCR material administered should be sufficient to effect, e.g., a therapeutic or prophylactic response, in the subject or animal over a reasonable time frame. For example, the dose of the inventive TCR material should be sufficient to bind to a cancer antigen, or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ is secreted by T cells expressing the inventive TCR, polypeptide, or protein upon administration of a given dose of such T cells to a mammal among a set of mammals of which is each given a different dose of the T cells, could be used to determine a starting dose to be administered to a mammal. The extent to which target cells are lysed or IFN-γ is secreted upon administration of a certain dose can be assayed by methods known in the art.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the condition being treated. In an embodiment in which the inventive TCR material is a population of cells, the number of cells administered per infusion may vary, e.g., from about $1 \times 10^6$ to about $1 \times 10^{12}$ cells or more. In certain embodiments, fewer than $1 \times 10^6$ cells may be administered.

It is contemplated that the inventive pharmaceutical compositions, TCRs, polypeptides, proteins, nucleic acids, recombinant expression vectors, host cells, or populations of cells can be used in methods of treating or preventing cancer. Without being bound to a particular theory or mechanism, the inventive TCRs are believed to bind specifically to KK-LC-1, such that the TCR (or related inventive polypeptide or protein), when expressed by a cell, is able to mediate an immune response against a target cell expressing KK-LC-1. In this regard, the invention provides a method of treating or preventing cancer in a mammal, comprising administering to the mammal any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, in an amount effective to treat or prevent cancer in the mammal.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the cancer being treated or prevented. For example, treatment or prevention can include promoting the regression of a tumor. Also, for purposes herein, "prevention" can encompass delaying the onset of the condition, or a symptom or condition thereof, or preventing recurrence of the cancer.

Also provided is a method of detecting the presence of cancer in a mammal. The method comprises contacting a sample comprising one or more cells from the mammal with any of the inventive TCRs, polypeptides, proteins, nucleic acids, recombinant expression vectors, host cells, populations of cells, or pharmaceutical compositions described herein, thereby forming a complex, and detecting the complex, wherein detection of the complex is indicative of the presence of cancer in the mammal, wherein the condition is cancer.

With respect to the inventive method of detecting cancer in a mammal, the sample of cells can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the mammal. Preferably, the contacting is in vitro.

Also, detection of the complex can occur through any number of ways known in the art. For instance, the inventive TCRs, polypeptides, proteins, nucleic acids, recombinant expression vectors, host cells, or populations of cells described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, esophageal cancer, uterine cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is cancer of the bladder, uterine cervix, stomach, breast, lung, colon, rectum, or pancreas. A particularly preferred cancer is carcinoma of the bladder, uterine cervix, stomach, breast, lung, colon, rectum, or pancreas. While the cancers most commonly associated with KK-LC-1 expression include cancer of the bladder, uterine cervix, stomach, breast, lung, colon, rectum, and pancreas, the inventive methods may be used to treat any KK-LC-1-positive cancer, including those that occur at other anatomical areas.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

Example 1

This example demonstrates the isolation of an anti-KK-LC-1 TCR.

A patient with cervical adenocarcinoma experienced complete regression of her metastatic disease following the administration of tumor-infiltrating lymphocytes (TIL) (TIL-3853). The TIL-3853 were subjected to IMMUNOSEQ (Adaptive Biotechnologies) analysis to identify the sequences of the TCRα and TCRβ chains in the administered T-cell repertoire. The administered T cells were mainly composed of one clonotype with an approximate frequency of 67% (TCRBV07-03/TCRAV35-01). The TCR comprised an alpha chain variable region amino acid sequence of SEQ ID NO: 9 and a beta chain variable region amino acid sequence of SEQ ID NO: 11. The junction region (CDR3 flanked by an amino acid residue on each side) of the alpha chain comprised the amino acid sequence of SEQ ID NO: 18. The junction region of the beta chain comprised the amino acid sequence of SEQ ID NO: 19.

Example 2

This example demonstrates the construction of a retroviral vector encoding the anti-KK-LC-1 TCR.

An MSGV1-retroviral vector was constructed which encoded TCR alpha and beta chain variable regions which were identical to those of the TCR of Example 1 with the exception that the amino acid residue at position 2 of the beta chain was changed from a glycine to an alanine in order to facilitate cloning into the vector. Additional modifications to the wild-type TCR were made, as described in more detail below.

The TCRβ VDJ regions were fused to a mouse TCRβ constant chain, and the TCRα VJ regions were fused to the mouse TCRα constant chain. Without being bound to a particular theory or mechanism, it is believed that replacing the constant regions of the human TCRα and TCRβ chains with murine constant regions improves TCR expression and functionality (Cohen et al., *Cancer Res.,* 66(17): 8878-86 (2006)).

In addition, the murine TCRα and TCRβ constant chains were cysteine-modified, and transmembrane hydrophobic mutations were introduced into the murine TCRα constant chain. Without being bound to a particular theory or mechanism, it is believed that these modifications result in preferential pairing of the introduced TCR chains and enhanced TCR surface expression and functionality (Cohen et al., *Cancer Res.,* 67(8):3898-903 (2007); Haga-Friedman et al., *J. Immu.,* 188: 5538-5546 (2012)).

After the modifications described in this Example were made, the full-length TCR alpha chain comprised the amino acid sequence of SEQ ID NO: 15 and the full-length TCR beta chain comprised the amino acid sequence of SEQ ID NO: 16.

The TCRβ and TCRα chains were separated by a Furin Ser/Gly P2A linker (SEQ ID NO: 17) to ensure a comparable expression efficiency of the two chains (Szymczak et al., *Nat. Biotechnol.,* 22(5):589-94 (2004)).

The final MSGV1 vector comprised an expression cassette comprising the nucleotide sequence of SEQ ID NO: 61 encoding the amino acid sequence of SEQ ID NO: 12. The expression cassette encoded, from the 5' to 3' end, the full-length TCR beta chain of SEQ ID NO: 16, the Furin Ser/Gly P2A linker of SEQ ID NO: 17, and the full-length TCR alpha chain of SEQ ID NO: 15. The expression cassette had the following configuration: 5'NotI-VDJβ-mCβ-Furin/SGSG/P2A-VJα-mCα-EcoRI3'.

Example 3

This example demonstrates TCR expression by peripheral blood T cells transduced with the vector of Example 2.

Retrovirus encoding the TCR was produced and used to transduce autologous peripheral blood T cells with the MSGV1 vector of Example 2. The expression of the introduced TCR was assessed by flow cytometry using an antibody specific for the mouse TCRβ chain constant region. Table 1 shows the percentage of untransduced (UT) and TCR-transduced T cells expressing CD8 and the murine TCR beta chain constant region (mTCRbeta).

TABLE 1

|  | Untransduced (UT) T cells | TCR-transduced T cells |
| --- | --- | --- |
| CD8+mTCRbeta+ | 0.1 | 42.6 |
| CD8−mTCRbeta− | 48.8 | 5.8 |
| CD8+mTCRbeta− | 51.0 | 15.1 |
| CD8−mTCRbeta+ | 0.1 | 36.6 |

Example 4

This example demonstrates the specificity of the TCR of Example 2.

The TCR-transduced T cells of Example 3 were tested for reactivity against a number of tumor antigens. Patient autologous antigen presenting cells (APC) were electroporated with RNA encoding KK-LC-1, GP100, or MAGEA3 tumor antigen (target cells). Control target cell APC were electroporated with RNA encoding green fluorescent protein (GFP). The APC target cells were co-cultured with the TCR-transduced T cells of Example 3 (effector cells). As controls, TCR-transduced T cells were cultured alone or were non-specifically stimulated with phorbol myristate acetate (PMA)/ionomycin. Reactivity was assessed by counting the number of interferon (IFN)-γ positive spots per 20,000 T cells (ELISPOT). The results are shown in Table 2.

TABLE 2

|  | UT T cells | TCR transduced T cells |
| --- | --- | --- |
| KK-LC-1 | <25 | >500 |
| GP100 | <25 | <25 |
| MAGEA3 | <25 | <25 |
| GFP | <25 | <25 |
| PMA/Ionomycin | >500 | >500 |
| T cells alone | <25 | <25 |

As shown in Table 2, the TCR-transduced T cells were reactive against the KK-LC-1 antigen, but not against other antigens tested. These results indicated that the introduced TCR recognized an epitope of KK-LC-1 presented in the context of a patient HLA molecule.

Example 5

This example demonstrates that the KK-LC-1 response in TIL-3853 is mediated by CD8+ T cells.

The TIL-3853 of Example 1 were also tested for reactivity against the KK-LC-1 antigen by measuring CD137 upregulation by flow cytometry. Tables 3 and 4 show the percentage of pre-treatment peripheral blood T cells from Patient 3853 (Table 3) and TIL-3853 (Table 4) (cells gated on CD3+ T cells) expressing CD8 and CD137 following treatment with the non-specific stimulator PMA/ionomycin or following co-culture with APC expressing KK-LC-1 or GFP.

TABLE 3

| peripheral blood T cells from Patient 3853 | KK-LC-1 | GFP | PMA/Ionomycin |
| --- | --- | --- | --- |
| CD137+CD8+ | 0.0 | 0.0 | 17.2 |
| CD137−CD8− | 76.2 | 84.5 | 47.4 |
| CD137+CD8− | 0.0 | 0.0 | 28.2 |
| CD137−CD8+ | 23.7 | 15.5 | 7.2 |

TABLE 4

| TIL-3853 | KK-LC-1 | GFP | PMA/Ionomycin |
| --- | --- | --- | --- |
| CD137+CD8+ | 34.5 | 0.2 | 86.8 |
| CD137−CD8− | 24.7 | 10.2 | 0.9 |
| CD137+CD8− | 0.2 | 0.1 | 12.0 |
| CD137−CD8+ | 40.6 | 89.5 | 0.3 |

The results indicated that the KK-LC-1 response in TIL-3853 was mediated by CD8+ T cells (% CD137+CD8+ T cells indicated in bold) (Tables 3 and 4). This finding suggested that the KK-LC-1 TCR was likely to be HLA-class I restricted.

Example 6

This example demonstrates that the TCR of Example 2 has antigenic specificity for KK-LC-1 presented in the context of a HLA-A*0101 molecule.

To identify the HLA-restriction element of the KK-LC-1 reactive TCR of Example 2, COS7 cells (target cells) were transfected with DNA encoding (i) no HLA molecule or one of patient 3853's six HLA-class I molecules (A*01:01, A*25:01, B*08:01, B*18:01, C*07:01, or C*12:03) and (ii) the KK-LC-1 antigen, control antigen MAGE-A3, control antigen GFP, or no antigen (FIG. 1A). T cells transduced with an HLA-A*0101 restricted TCR targeting MAGE-A3$^{168-176}$ and untransduced T cells (UT) were used as control effector cells. The target cells were co-cultured with the control effector cells or effector T cells transduced with the TCR of Example 2. As controls, COS7 cells were cultured alone, UT and TCR transduced T cells were cultured alone, and UT and TCR transduced T cells were non-specifically stimulated with PMA/ionomycin. IFN-γ released in supernatants was measured. The results are shown in FIG. 1A.

As shown in FIG. 1A, the anti-KK-LC-1 TCR of Example 2 specifically recognized the KK-LC-1 antigen in the context of the HLA-A*0101 molecule.

Example 7

This example demonstrates that the minimal epitope of KK-LC-1 targeted by the HLA-A*0101 restricted anti-KK-LC-1 TCR of Example 2 is situated between residues 49 and 67 of the KK-LC-1 protein.

Figure 1B:
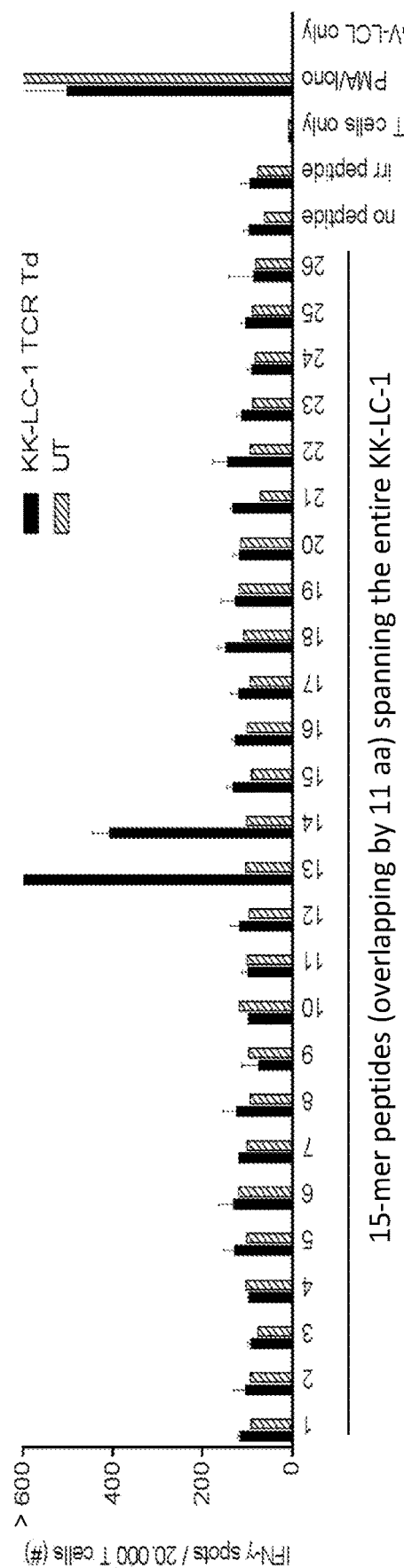
FIG. 1B is a graph showing the number of IFN-γ-positive spots per 20,000 T cells observed upon co-culture of autologous APC (target cells) pulsed with one of peptide numbers 1-26 (SEQ ID NOs: 20-45, respectively), no peptide, or irrelevant peptide with untransduced (UT) T cells (striped bars) or T cells transduced with the vector of Example 2 encoding an anti-KK-LC-1 TCR (black bars). UT T cells, anti-KK-LC-1 TCR transduced T cells and autologous APC (EBV-LCL target cells) cultured alone served as negative controls. UT T cells and anti-KK-LC-1 TCR transduced T cells non-specifically stimulated with PMA/ionomycin served as positive controls.

To identify the epitope targeted by the KK-LC-1 reactive TCR, 15-mer peptides overlapping by 11 amino acids, spanning the entire KK-LC-1 protein were synthesized (Table 5). Each peptide was pulsed individually on autologous APC (target cells) and tested for recognition by autologous peripheral blood T cells transduced with the TCR of Example 2 (effector cells) by IFN-γ ELISPOT. Autologous APC pulsed with no peptide or irrelevant peptide served as control target cells. UT T cells, anti-KK-LC-1 TCR transduced T cells and autologous APC (EBV-LCL target cells) cultured alone, and UT T cells and anti-KK-LC-1 TCR transduced T cells non-specifically stimulated with PMA/ionomycin, served as controls. Untransduced T cells were used as a control effector cell, and these control effector cells did not show recognition of any of the peptides (FIG. 1B). Crude peptides in Table 5 were synthesized by Genscript.

TABLE 5

Peptides (15-mers, overlapping by 11 amino acids) spanning the entire KK-LC-1 protein

| Peptide No. | Amino acid position in KK-LC-1 protein START | END | Peptide | SEQ ID NO: |
|---|---|---|---|---|
| 1 | 1 | 15 | MNFYLLLASSILCAL | 20 |
| 2 | 5 | 19 | LLLASSILCALIVFW | 21 |
| 3 | 9 | 23 | SSILCALIVFWKYRR | 22 |
| 4 | 13 | 27 | CALIVFWKYRRFQRN | 23 |
| 5 | 17 | 31 | VFWKYRRFQRNTGEM | 24 |
| 6 | 21 | 35 | YRRFQRNTGEMSSNS | 25 |
| 7 | 25 | 39 | QRNTGEMSSNSTALA | 26 |
| 8 | 29 | 43 | GEMSSNSTALALVRP | 27 |
| 9 | 33 | 47 | SNSTALALVRPSSSG | 28 |
| 10 | 37 | 51 | ALALVRPSSSGLINS | 29 |
| 11 | 41 | 55 | VRPSSSGLINSNTDN | 30 |
| 12 | 45 | 59 | SSGLINSNTDNNLAV | 31 |
| 13 | 49 | 63 | INSNTDNNLAVYDLS | 32 |
| 14 | 53 | 67 | TDNNLAVYDLSRDIL | 33 |
| 15 | 57 | 71 | LAVYDLSRDILNNFP | 34 |
| 16 | 61 | 75 | DLSRDILNNFPHSIA | 35 |
| 17 | 65 | 79 | DILNNFPHSIARQKR | 36 |
| 18 | 69 | 83 | NFPHSIARQKRILVN | 37 |
| 19 | 73 | 87 | SIARQKRILVNLSMV | 38 |
| 20 | 77 | 91 | QKRILVNLSMVENKL | 39 |
| 21 | 81 | 95 | LVNLSMVENKLVELE | 40 |
| 22 | 85 | 99 | SMVENKLVELEHTLL | 41 |
| 23 | 89 | 103 | NKLVELEHTLLSKGF | 42 |
| 24 | 93 | 107 | ELEHTLLSKGFRGAS | 43 |
| 25 | 97 | 111 | TLLSKGFRGASPHRK | 44 |
| 26 | 99 | 113 | LSKGFRGASPHRKST | 45 |

As shown in FIG. 1B, the T cells transduced with the TCR of Example 2 recognized two 15-mer peptides corresponding to amino acid residue positions 49-63 (INSNTDNNLAVYDLS) (SEQ ID NO: 32) and 53-67 (TDNNLAVYDLSRDIL) (SEQ ID NO: 33) of the KK-LC-1 protein (FIG. 1B). This result indicated that the minimal epitope of KK-LC-1 targeted by the HLA-A*0101 restricted anti-KK-LC-1 TCR of Example 2 was situated between residues 49 and 67 of the KK-LC-1 protein.

Example 8

This example demonstrates that KK-LC-1$^{52-60}$ (NTDNNLAVY) (SEQ ID NO: 2) is the likely minimal epitope targeted by the T cells transduced with the HLA-A*0101 restricted anti-KK-LC-1 TCR of Example 2.

To further define the minimal epitope of KK-LC-1 targeted by the HLA-A*0101 restricted KK-LC-1 reactive TCR, peptide prediction algorithms (iedb.org) were used to predict the best binding peptides of KK-LC-1 in HLA-A*0101. The prediction algorithm indicated that a 9-mer peptide 52-60 (NTDNNLAVY) (SEQ ID NO: 2) displayed the highest affinity among all predicted 8-, 9-, 10- and 11-mer peptides of KK-LC-1 in HLA-A*0101 (Table 6). In addition to the best predicted 9-mer peptide, a shorter 8-mer (NTDNNLAV) (SEQ ID NO: 46), a longer 10-mer (NTDNNLAVYD) (SEQ ID NO: 52), and a longer 11-mer (NTDNNLAVYDL) (SEQ ID NO: 48) peptide version of this 9-mer peptide were synthesized (Table 7).

TABLE 6

Top-10 predicted minimal epitopes of KK-LC-1$^{49-67}$ in HLA-A*0101

| Allele | Length | Amino acid Position Start | End | Peptide | Affinity (nM) | Rank (%-tile) |
|---|---|---|---|---|---|---|
| HLA-A*01:01 | 9 | 52 | 60 | NTDNNLAVY (SEQ ID NO: 2) | 6 | 0.2 |
| HLA-A*01:01 | 8 | 52 | 59 | NTDNNLAV (SEQ ID NO: 46) | 45 | 20.1 |
| HLA-A*01:01 | 11 | 50 | 60 | NSNTDNNLAVY (SEQ ID NO: 47) | 82 | 1 |

TABLE 6-continued

Top-10 predicted minimal epitopes of
KK-LC-1^49-67 in HLA-A*0101

| Allele | Length | Position Start | Position End | Peptide | Affinity (nM) | Rank (%-tile) |
|---|---|---|---|---|---|---|
| HLA-A*01:01 | 11 | 52 | 62 | NTDNNLAVYDL (SEQ ID NO: 48) | 1365 | 26.35 |
| HLA-A*01:01 | 10 | 51 | 60 | SNTDNNLAVY (SEQ ID NO: 49) | 6422 | 2.25 |
| HLA-A*01:01 | 9 | 50 | 58 | NSNTDNNLA (SEQ ID NO: 50) | 7686 | 1.85 |
| HLA-A*01:01 | 10 | 50 | 59 | NSNTDNNLAV (SEQ ID NO: 51) | 9259 | 7.45 |
| HLA-A*01:01 | 10 | 52 | 61 | NTDNNLAVYD (SEQ ID NO: 52) | 10746 | 2.95 |
| HLA-A*01:01 | 8 | 53 | 60 | TDNNLAVY (SEQ ID NO: 53) | 15847 | 28.15 |
| HLA-A*01:01 | 8 | 50 | 57 | NSNTDNNL (SEQ ID NO: 54) | 18350 | 7.7 |

Table 6: The MHC-class I predications were made using the IEDB analysis resource ANN tool (Nielsen et al., *Protein Sci.*, 12: 1007-1017 (2003); Lundegaard et al., *Nucleic Acids Res.*, 36: W509-512 (2008)). Affinity <50 nM is considered high. The 9-mer peptide NTDNNLAVY (SEQ ID NO: 2) displayed the highest affinity and lowest percentile rank among all 8-mer, 9-mer, 10-mer, and 11-mer peptides of amino acid residue positions 49-67 of KK-LC-1, as well as of the full-length KK-LC-1 amino acid sequence predicated to bind in HLA-A*0101. Only top 10 best predicted minimal epitopes are shown.

TABLE 7

Analyzed predicted minimal
epitopes of KK-LC-1

| Allele | Length | Amino acid Position | Peptide | Affinity (nM) | Rank (%-tile) |
|---|---|---|---|---|---|
| HLA-A*01:01 | 8 | 52-59 | NTDNNLAV (SEQ ID NO: 46) | 45 | 0.2 |
| HLA-A*01:01 | 9 | 52-60 | NTDNNLAVY (SEQ ID NO: 2) | 6 | 0.2 |
| HLA-A*01:01 | 10 | 52-61 | NTDNNLAVYD (SEQ ID NO: 52) | 10746 | 3.4 |
| HLA-A*01:01 | 11 | 52-62 | NTDNNLAVYDL (SEQ ID NO: 48) | 1365 | 0.7 |

Table 7: The MHC-class I predications were made using the IEDB analysis resource ANN tool (Nielsen et al., *Protein Sci.*, 12: 1007-1017 (2003); Lundegaard et al., *Nucleic Acids Res.*, 36: W509-512 (2008)). Affinity <50 nM is considered high. The 9-mer peptide NTDNNLAVY (SEQ ID NO: 2) displayed the highest affinity and lowest percentile rank among all 8-mer, 9-mer, 10-mer, and 11-mer peptides of amino acid residue positions 49-67 of KK-LC-1, as well as of the full-length KK-LC-1 amino acid sequence predicated to bind in HLA-A*0101. Length variations of this 9-mer peptide (8-, 10-, and 11-mer) were included in the analysis. Peptides were synthesized by Genscript at >90% purity.

The peptides in Table 7 were tested for recognition by T cells transduced with the HLA-A*0101 restricted anti-KK-LC-1 TCR of Example 2 by IFN-γ ELISPOT. Autologous APC (target cells) were pulsed with 0, 0.0001, 0.001, 0.01, 0.1, 1, or 10 μM of 8-mer, 9-mer, 10-mer, or 11-mer. The target cells were co-cultured with T cells transduced with the HLA-A*0101 restricted anti-KK-LC-1 TCR of Example 2 (effector cells). Untransduced T cells were used as a control effector cell. UT T cells, anti-KK-LC-1 TCR transduced T cells and autologous APC (EBV-LCL target cells) cultured alone, and UT T cells and anti-KK-LC-1 TCR transduced T cells non-specifically stimulated with PMA/ionomycin, served as controls.

Figure 1C:
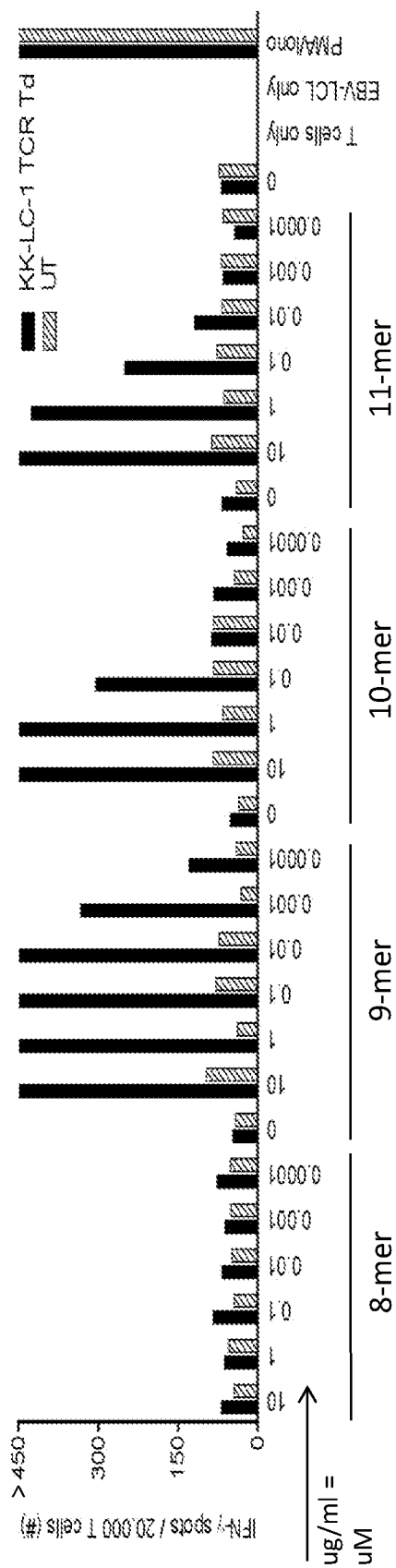
FIG. 1C is a graph showing the number of IFN-γ-positive spots per 20,000 T cells observed upon co-culture of autologous APC (target cells) pulsed with 0, 0.0001, 0.001, 0.01, 0.1, 1, or 10 μM of 8-mer (SEQ ID NO: 46), 9-mer (SEQ ID NO: 2), 10-mer (SEQ ID NO: 52), or 11-mer (SEQ ID NO: 48) peptide upon co-culture with T cells transduced with the vector of Example 2 encoding an anti-KK-LC-1 TCR (black bars) or untransduced (UT) T cells (striped bars). UT T cells, anti-KK-LC-1 TCR transduced T cells and autologous APC (EBV-LCL target cells) cultured alone served as negative controls. UT T cells and anti-KK-LC-1 TCR transduced T cells non-specifically stimulated with PMA/ionomycin served as positive controls.

The results are shown in FIG. 1C. T cells transduced with the HLA-A*0101 restricted anti-KK-LC-1 TCR of Example 2 showed no recognition of the 8-mer peptide pulsed APC, but recognized the 9-, 10- and 11-mer peptide pulsed APC. The strongest reactivity was observed against the 9-mer peptide pulsed APC (FIG. 1C). Functional avidity of the KK-LC-1$^{52-60}$ TCR transduced T cells appeared to be in the range of $10^{-9}$-$10^{-10}$ M KK-LC-1$^{52-60}$ peptide, suggesting high functional avidity of this TCR. These results identified KK-LC-1$^{52-60}$ epitope NTDNNLAVY (SEQ ID NO: 2) as the likely minimal epitope targeted by the T cells transduced with the HLA-A*0101 restricted anti-KK-LC-1 TCR of Example 2, and indicated that this TCR displayed high functional avidity.

Example 9

This example demonstrates that the anti-KK-LC-1$^{52-60}$ TCR of Example 2 can recognize KK-LC-1 antigen naturally processed and presented by tumor cell lines in the context of HLA-A*0101.

To evaluate whether T cells transduced with the anti-KK-LC-1 TCR of Example 2 (effector cells) could recognize tumor cell lines naturally expressing the KK-LC-1 antigen in the context of HLA-A*0101 (target cells), a variety of tumor cell lines derived from different cancer histologies were tested for recognition. Untransduced T cells and unrelated donor T cells transduced with a TCR targeting MAGE-A3$^{168-176}$ in the context of HLA-A*0101 were used as control effector cells. The expression level of KK-LC-1 and MAGE-A3 mRNA in the tumor cell lines was derived from the GENEVESTIGATOR database (indicated as high or low), and the HLA typing of the cell lines is described in Adams et al., *J. Transl. Med.*, 3(1):11 (2005) (Table 8).

TABLE 8

| Cell line | Histology | HLA-A1+/− | KK-LC-1 high/low | MAGE-A3 high/low |
|---|---|---|---|---|
| EKVX | Lung adenocarcinoma | + | High | High |
| HCT-116 | Colon carcinoma | + | Low | High |
| HeLa | Cervical adenocarcinoma | − | High | High |
| DU145 | Prostate cancer | − | High | Low |

The target tumor cell lines in Table 8 were transfected with (i) HLA-A*0101 and KK-LC-1, (ii) KK-LC-1, (iii) HLA-A*0101 and MAGE-A3, (iv) MAGE-A3, (v) HLA-A*0101, or (vi) none of (i)-(v) to investigate whether the HLA and/or KK-LC-1 overexpression may be limiting tumor cell line recognition by the T cells transduced with the anti-KK-LC-1 TCR of Example 2. The target cells were co-cultured with effector cells and IFN-γ was measured. Effector T cells cultured alone served as a control. The results are shown in FIGS. 2A-2D.

Figure 2A:
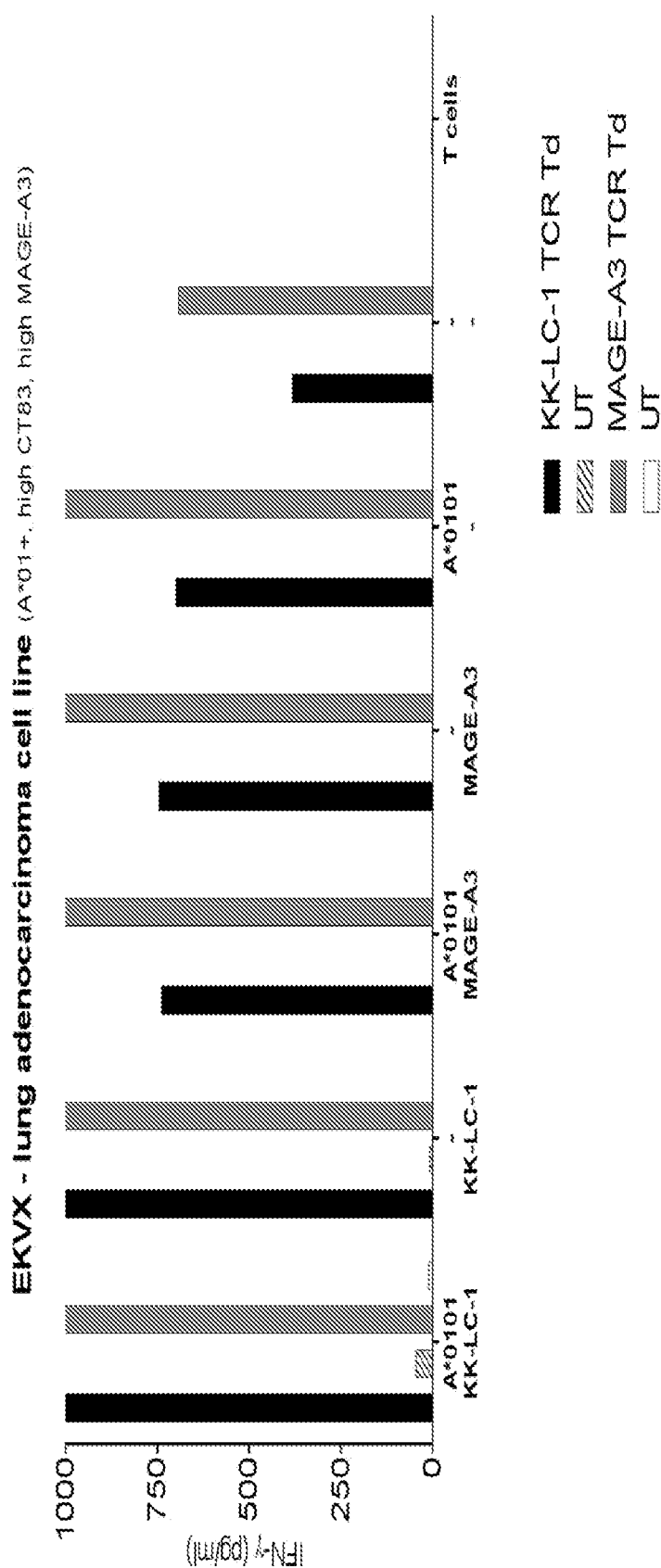
FIG. 2A is a graph showing the concentration of IFN-γ (pg/ml) secreted by untransduced (UT) effector cells (unshaded bars and striped bars), T cells transduced with a HLA-A*0101 restricted TCR targeting MAGE-A3$^{168-176}$ (grey bars), or T cells transduced with the vector of Example 2 encoding an anti-KK-LC-1 TCR (black bars) upon co-culture with target tumor cell line EKVX transfected with (i) HLA-A*0101 and KK-LC-1, (ii) KK-LC-1, (iii) HLA-A*0101 and MAGE-A3, (iv) MAGE-A3, (v) HLA-A*0101, or (vi) none of (i)-(v). T cells cultured alone served as a control.
Figure 2B:
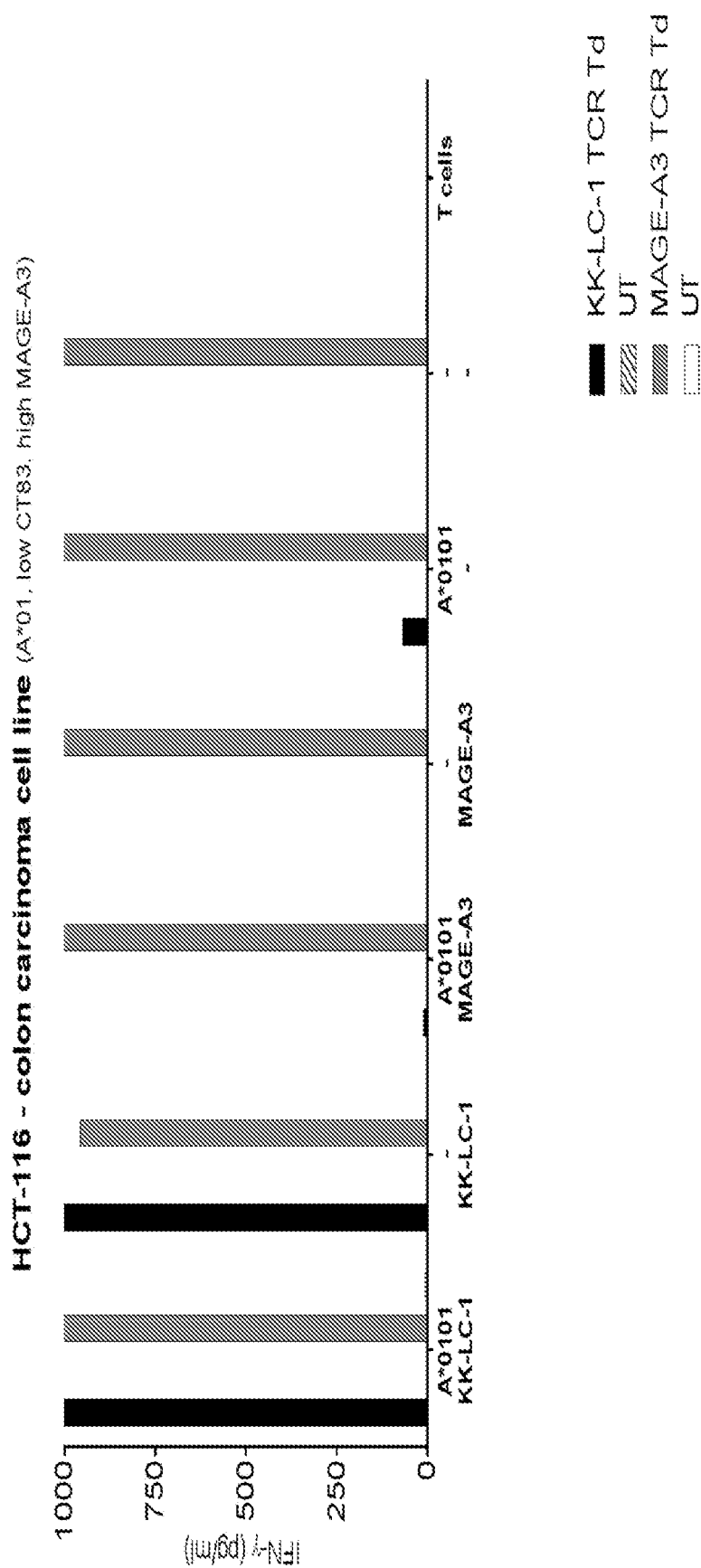
FIG. 2B is a graph showing the concentration of IFN-γ (pg/ml) secreted by untransduced (UT) effector cells (unshaded bars and striped bars), T cells transduced with a HLA-A*0101 restricted TCR targeting MAGE-A3$^{168-176}$ (grey bars), or T cells transduced with the vector of Example 2 encoding an anti-KK-LC-1 TCR (black bars) upon co-culture with target tumor cell line HCT-116 transfected with (i) HLA-A*0101 and KK-LC-1, (ii) KK-LC-1, (iii) HLA-A*0101 and MAGE-A3, (iv) MAGE-A3, (v) HLA-A*0101, or (vi) none of (i)-(v). T cells cultured alone served as a control.
Figure 2C:
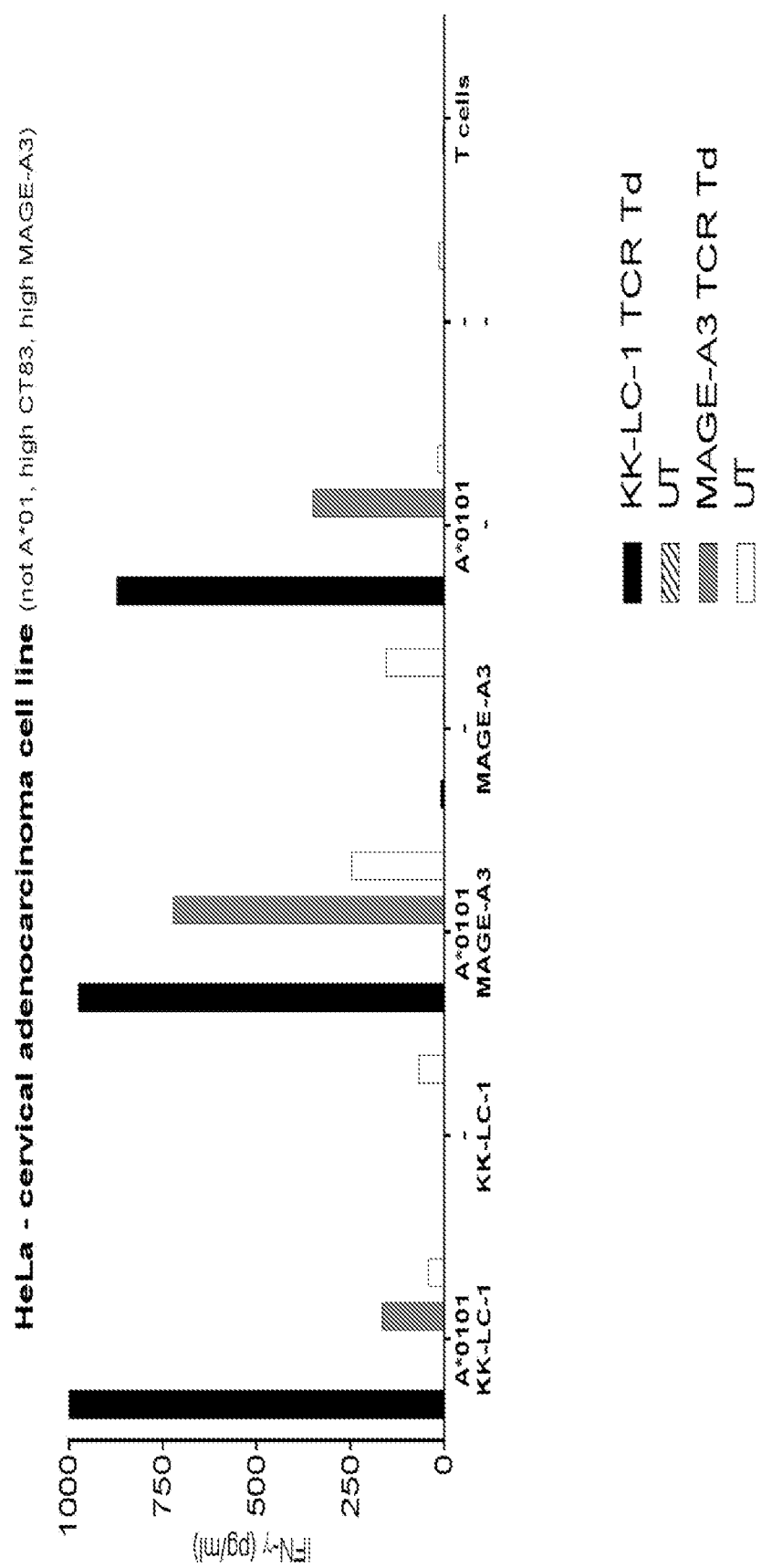
FIG. 2C is a graph showing the concentration of IFN-γ (pg/ml) secreted by untransduced (UT) effector cells (unshaded bars and striped bars), T cells transduced with a HLA-A*0101 restricted TCR targeting MAGE-A3$^{168-176}$ (grey bars), or T cells transduced with the vector of Example 2 encoding an anti-KK-LC-1 TCR (black bars) upon co-culture with target tumor cell line HeLa transfected with (i) HLA-A*0101 and KK-LC-1, (ii) KK-LC-1, (iii) HLA-A*0101 and MAGE-A3, (iv) MAGE-A3, (v) HLA-A*0101, or (vi) none of (i)-(v). T cells cultured alone served as a control.
Figure 2D:
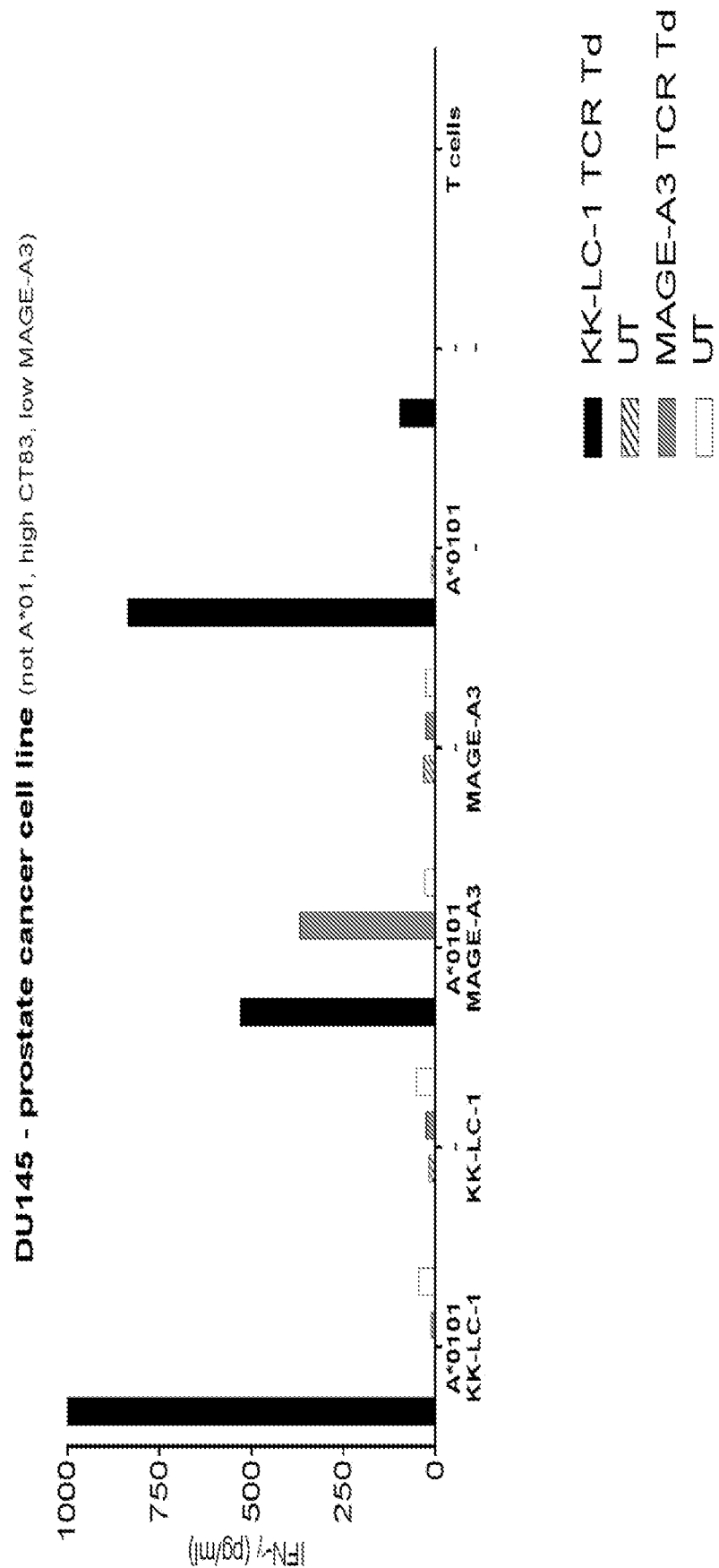
FIG. 2D is a graph showing the concentration of IFN-γ (pg/ml) secreted by untransduced (UT) effector cells (unshaded bars and striped bars), T cells transduced with a HLA-A*0101 restricted TCR targeting MAGE-A3$^{168-176}$ (grey bars), or T cells transduced with the vector of Example 2 encoding an anti-KK-LC-1 TCR (black bars) upon co-culture with target tumor cell line DU145 transfected with (i) HLA-A*0101 and KK-LC-1, (ii) KK-LC-1, (iii) HLA-A*0101 and MAGE-A3, (iv) MAGE-A3, (v) HLA-A*0101, or (vi) none of (i)-(v). T cells cultured alone served as a control.

KK-LC-1$^{52-60}$ reactive TCR transduced T cells were capable of recognizing tumor cell lines with high expression of KK-LC-1 mRNA (FIG. 2A, 2C, 2D; EKVX, HeLa and DU145), but not a tumor cell line with low expression of KK-LC-1 mRNA (FIG. 2B; HCT-116). While EKVX is HLA-A*0101+ and was recognized by KK-LC-1$^{52-60}$ reactive TCR transduced T cells, HeLa and DU145 are HLA-A*0101 negative, and these tumor cell lines were only recognized by the KK-LC-1$^{52-60}$ reactive TCR after transfection with HLA-A*0101, confirming HLA-A*0101 restricted recognition of this TCR. Furthermore, low KK-LC-1, rather than HLA, expression was shown to be the limiting factor in the recognition of the HCT-116 tumor cell line, as the overexpression of KK-LC-1, but not HLA-A*0101, by transfection, conferred recognition of this tumor cell line by the KK-LC-1$^{52-60}$ reactive TCR transduced T cells. These results indicate that KK-LC-1$^{52-60}$ TCR can recognize KK-LC-1 antigen naturally processed and presented by tumor cell lines in the context of HLA-A*0101.

Example 10

This example demonstrates the expression of KK-LC-1 in a variety of tumor cell lines.

To enable characterization of the anti-KK-LC-1 TCR with respect to recognition of unmanipulated tumors, the expression level of the CT83 gene encoding the KK-LC-1 antigen was determined in a variety of tumor cell lines by real-time quantitative reverse transcription polymerase chain reaction (qRT-PCR).

RNA was extracted from tumor cell lines using RNEASY PLUS MICRO microprep kit (Qiagen, Venlo, Netherlands). cDNA was made using QSCRIPT CDNA SUPERMIX kit (Quanta Bio, Beverly, Mass.). Subsequently, expression of the CT83 gene (encoding for the KK-LC-1 antigen) in tumor cell lines was determined by real-time quantitative reverse transcription polymerase chain reaction (qRT-PCR) with TAQMAN primer/probe sets specific for the CT83 gene (Hs02386421_g1, Thermo Fischer Scientific, Waltham, Mass.) and the housekeeping ACTB gene (Hs99999903_m1, Thermo Fischer Scientific) using the QUANTSTUDIO 3 RT-PCR system (Applied Biosystems, Grand Island, N.Y.) and following the manufacturer's standard instructions and thermal cycling conditions. Serially diluted DNA plasmids of CT83 and ACTB were used to generate standard curves for copy number quantification using standard procedures.

Figure 3:
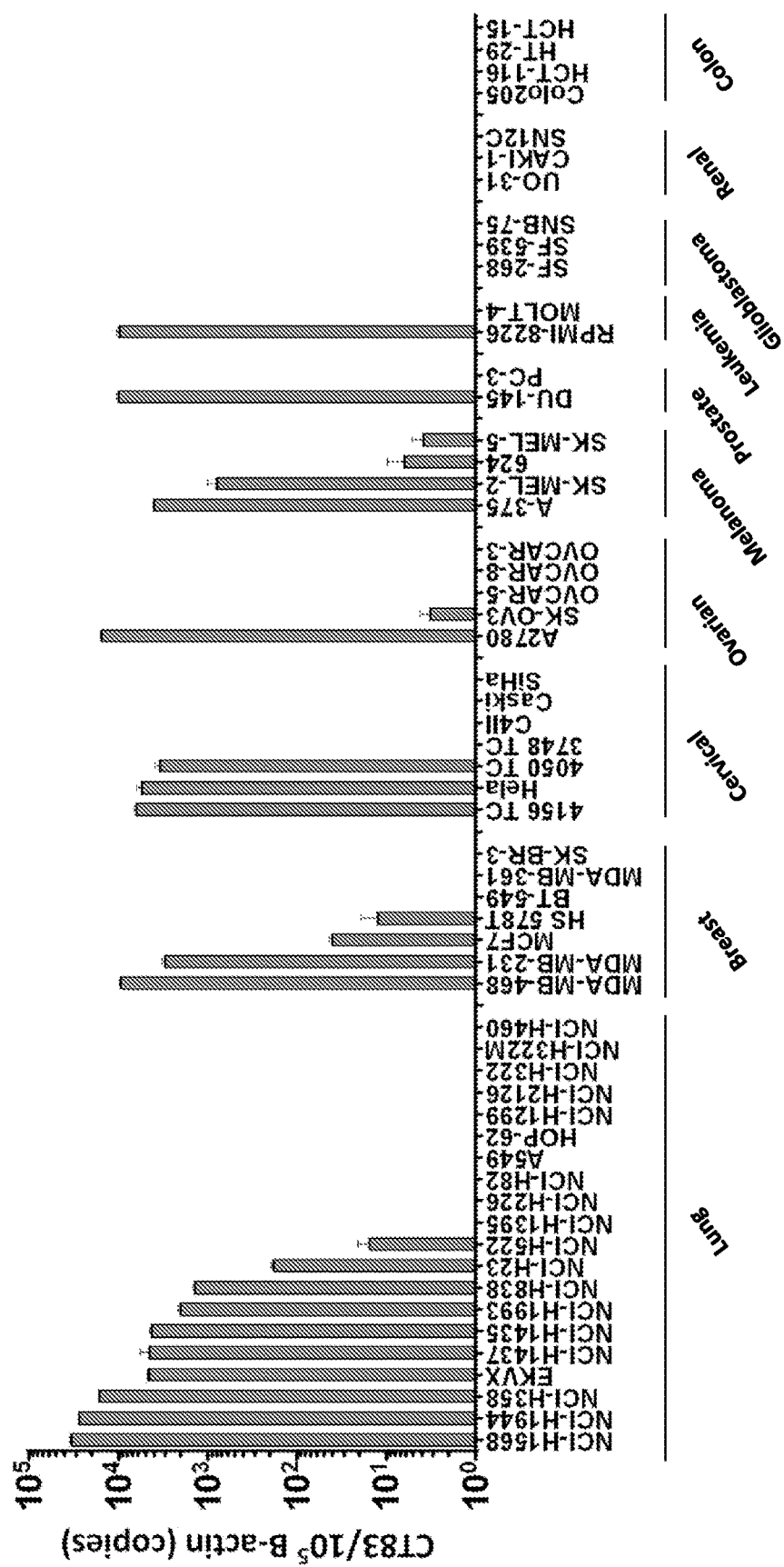
FIG. 3 is a graph showing the quantity of KK-LC-1 mRNA expression (CT83/10$^5$ β-actin (copies)) by cancer cell lines from different histologies.

The results are shown in FIG. 3. Numerous tumor cell lines (25 out of 47) from various cancer histologies were identified that expressed variable mRNA levels of KK-LC-1. Three tumor cell lines expressed KK-LC-1 as well as the pertinent HLA-A*01:01 restriction element, enabling testing of the HLA-A*01:01 restricted KK-LC-1$^{52-60}$ TCR for tumor recognition.

Example 11

This example demonstrates that the KK-LC-1 TCR of Example 2 recognizes and lyses tumor cell lines.

To further characterize the KK-LC-1-specific TCR, cytokine production as well as cytolytic activity of T cells transduced with the KK-LC-1-specific TCR of Example 2 were assessed upon co-culture with unmanipulated tumor cell lines.

Figure 4A:
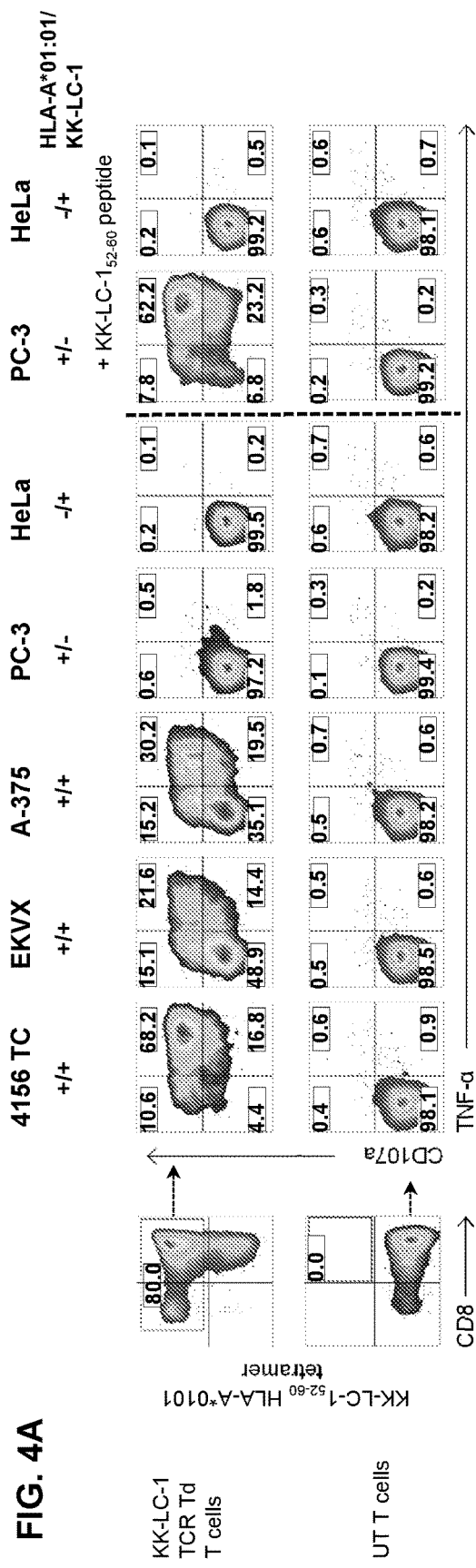
FIG. 4A includes flow cytometry plots. The values in the quadrants of the center panels show the percentages of cells expressing (or not expressing) CD107a and TNF-α upon co-culture of effector cells (KK-LC-1 TCR transduced (Td) or untransduced (UT) T cells) with target cells (the indicated unmanipulated tumor cell lines). The presence (+) or absence (−) of endogenously expressed HLA-A*0101 and/or KK-LC-1 by the tumor cells lines is indicated at the top of the figure. The values in the quadrants of the panels to the right of the dotted line show the percentages of cells expressing (or not expressing) CD107a and TNF-α upon co-culture of the same effector cells with target tumor cell lines PC-3 or HeLa pre-incubated with 0.1 μg/ml KK-LC-1$_{52-60}$ cognate peptide. The far left panels show that the data for the KK-LC-1 TCR Td T cells were gated on KK-LC-1$_{52-60}$ tetramer T cells (far left, arrow), and the data for UT T cells were gated on all CD3$^+$ T cells (far left, arrow).

Peripheral blood KK-LC-1 TCR-transduced (Td) and untransduced (UT) T cells were co-cultured for 6 hours with the indicated unmanipulated tumor cell lines (FIG. 4A), and flow cytometry was used to assess expression of the cytotoxic degranulation marker CD107a (LAMP-1) and TNF-α production by intracellular staining. The presence (+) or absence (−) of endogenously expressed HLA-A*0101 and/or KK-LC-1 is indicated in the top row of FIG. 4A. Tumor cell lines PC-3 and HeLa pre-incubated with 0.1 μg/ml KK-LC-1$_{52-60}$ cognate peptide (FIG. 4A, right) were also used as target cells. Data for KK-LC-1 TCR Td T cells were gated on KK-LC-1$_{52-60}$ tetramer T cells (FIG. 4A, far left, arrow). Data for UT T cells were gated on all CD3$^+$ T cells (FIG. 4A, far left, arrow). The tumor cell line histologies included 4156 TC and HeLa: cervical carcinoma, EKVX: lung carcinoma; A375: melanoma; PC-3: prostate carcinoma.

The results are shown in FIG. 4A. The KK-LC-1-specific TCR-transduced T cells produced the inflammatory effector cytokine TNF-α and mobilized the cytotoxic degranulation marker CD107a (LAMP-1) when co-cultured with tumor cells expressing KK-LC-1 and HLA-A*01:01 but not when co-cultured with tumor cells lacking the target antigen or restriction element (FIG. 4A).

In addition, specific cytolysis of the unmanipulated tumor cell lines described in this Example by the KK-LC-1 TCR Td T cells and UT T cells was measured by a cytotoxicity assay after a 6 hour co-culture.

Figure 4B:
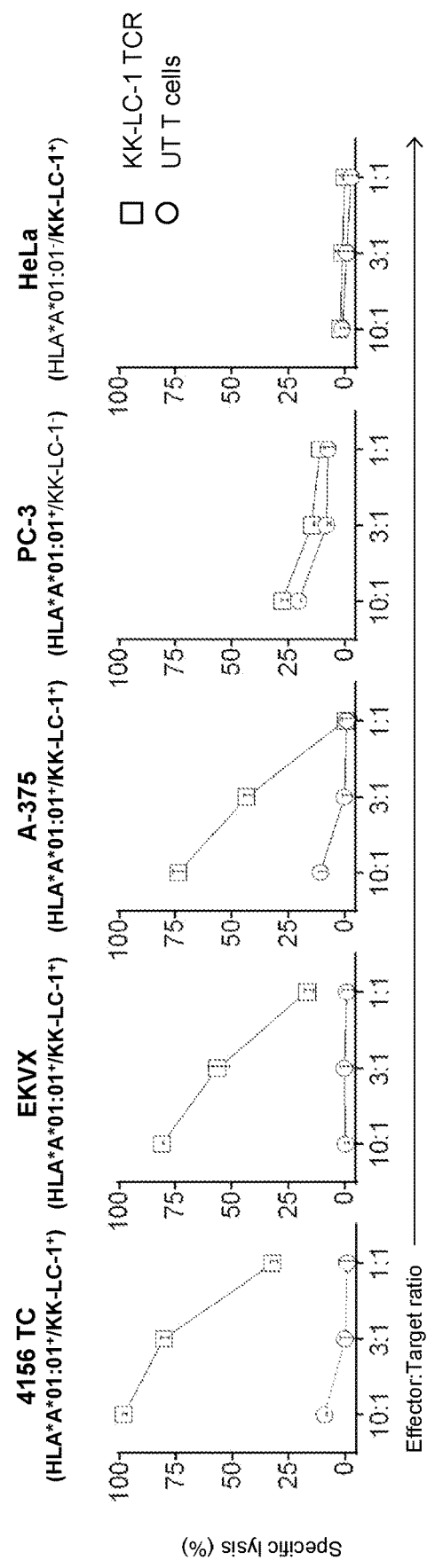
FIG. 4B includes graphs showing the percentage (%) of specific lysis of the target cells (the unmanipulated tumor cell lines of FIG. 4A) by effector cells (the KK-LC-1 TCR-transduced T cells (squares) or UT T cells (circles)) at the indicated effector to target ratios. The presence (+) or absence (−) of endogenously expressed KK-LC-1 and/or HLA-A*0101 by the tumor cell lines is indicated. Error bars represent standard deviation of triplicate wells.

The results are shown in FIG. 4B. The KK-LC-1-specific TCR transduced T cells displayed specific cytolysis of tumor cell lines in an antigen- and HLA-dependent manner in the cytotoxicity assay (FIG. 4B). These results indicated that the KK-LC-1-specific TCR of Example 2 displays antigen- and HLA-dependent recognition and killing of unmanipulated tumor cell lines.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A single isolated or purified nucleic acid comprising a nucleotide sequence encoding a T cell receptor (TCR), wherein the TCR has antigenic specificity for Kita-Kyushu Lung Cancer Antigen $1_{52-60}$ (KK-LC-$1_{52-60}$) presented by human leukocyte antigen (HLA)-A1,
wherein the TCR comprises the amino acid sequences of SEQ ID NOs: 3-8.

2. The nucleic acid according to claim 1, wherein the TCR comprises a murine constant region.

3. The nucleic acid according to claim 1, wherein the TCR comprises the amino acid sequences of:
(a) SEQ ID NO: 9 and
(b) SEQ ID NO: 10, wherein X at position 2 is Ala or Gly.

4. The nucleic acid according to claim 1, wherein the TCR further comprises the amino acid sequences of:
(a) SEQ ID NO: 13, wherein:
  (i) X at position 48 is Thr or Cys;
  (ii) X at position 112 is Ser, Gly, Ala, Val, Leu, Ile, Pro, Phe, Met, or Trp;
  (iii) X at position 114 is Met, Gly, Ala, Val, Leu, Ile, Pro, Phe, Met, or Trp; and
  (iv) X at position 115 is Gly, Ala, Val, Leu, Ile, Pro, Phe, Met, or Trp; and (b) SEQ ID NO: 14, wherein X at position 57 is Ser or Cys.

5. The nucleic acid according to claim 1, wherein the TCR comprises the amino acid sequences of SEQ ID NO: 15 and SEQ ID NO: 16.

6. A single isolated or purified nucleic acid comprising a nucleotide sequence encoding a polypeptide, wherein the polypeptide comprises a TCR alpha chain amino acid sequence comprising the amino acid sequences of SEQ ID NO: 3-5 and a TCR beta chain amino acid sequence comprising the amino acid sequences of SEQ ID NO: 6-8.

7. The nucleic acid according to claim 6, wherein the polypeptide comprises the amino acid sequence of:
(a) SEQ ID NO: 9 and
(b) SEQ ID NO: 10, wherein X at position 2 is Ala or Gly.

8. The nucleic acid according to claim 6, wherein the polypeptide further comprises the amino acid sequences of:
(a) SEQ ID NO: 13, wherein:
  (i) X at position 48 is Thr or Cys;
  (ii) X at position 112 is Ser, Gly, Ala, Val, Leu, Ile, Pro, Phe, Met, or Trp;
  (iii) X at position 114 is Met, Gly, Ala, Val, Leu, Ile, Pro, Phe, Met, or Trp; and (b) SEQ ID NO: 14, wherein X at position 57 is Ser or Cys.

9. The nucleic acid according to claim 6, wherein the polypeptide comprises the amino acid sequences of SEQ ID NO: 15 and SEQ ID NO: 16.

10. A single isolated or purified nucleic acid comprising a nucleotide sequence encoding a protein, wherein the protein comprises a first polypeptide chain comprising a TCR alpha chain amino acid sequence comprising the amino acid sequences of SEQ ID NOs: 3-5 and a second polypeptide chain comprising a TCR beta chain amino acid sequence comprising the amino acid sequences of SEQ ID NOs: 6-8.

11. The nucleic acid of claim 10, wherein the protein comprises:
   a first polypeptide chain comprising the amino acid sequence of SEQ ID NO: 9 and
   a second polypeptide chain comprising the amino acid sequence of SEQ ID NO: 10, wherein X at position 2 of SEQ ID NO: 10 is Ala or Gly.

12. The nucleic acid of claim 10, wherein:
   (a) the first polypeptide chain further comprises the amino acid sequence of SEQ ID NO: 13, wherein:
      (i) X at position 48 is Thr or Cys;
      (ii) X at position 112 is Ser, Gly, Ala, Val, Leu, Ile, Pro, Phe, Met, or Trp;
      (iii) X at position 114 is Met, Gly, Ala, Val, Leu, Ile, Pro, Phe, Met, or Trp; and
      (iv) X at position 115 is Gly, Ala, Val, Leu, Ile, Pro, Phe, Met, or Trp; and
   (b) the second polypeptide chain further comprises the amino acid sequence of SEQ ID NO: 14, wherein X at position 57 is Ser or Cys.

13. The nucleic acid according to claim 10, wherein the protein comprises a first polypeptide chain comprising the amino acid sequence of SEQ ID NO: 15 and a second polypeptide chain comprising the amino acid sequence of SEQ ID NO: 16.

14. The nucleic acid according to claim 6, wherein the polypeptide further comprises a linker comprising the amino acid sequence of SEQ ID NO: 17.

15. An isolated or purified TCR encoded by the nucleic acid according to claim 2.

16. A recombinant expression vector comprising the nucleic acid of claim 1.

17. The recombinant expression vector according to claim 16, wherein the nucleotide sequence encoding the beta chain is positioned 5' of the nucleotide sequence encoding the alpha chain.

18. A host cell comprising the recombinant expression vector of claim 16.

19. A population of cells comprising more than one host cell of claim 18.

20. A pharmaceutical composition comprising the population of cells according to claim 19, and a pharmaceutically acceptable carrier.

21. A method of detecting the presence of cancer in a human, comprising:
   (a) contacting a sample comprising one or more cells from the human with a population of host cells, thereby forming a complex, and
   (b) detecting the complex, wherein detection of the complex is indicative of the presence of cancer in the human,
   wherein the population of host cells expresses an isolated or purified nucleic acid and the cancer expresses HLA-A1 and KK-LC-$1_{52-60}$,
   wherein the nucleic acid comprises a nucleotide sequence encoding a TCR, wherein the TCR has antigenic specificity for KK-LC-$1_{52-60}$ presented by HLA-A1, and
   wherein the TCR comprises the amino acid sequences of SEQ ID NOs: 3-8.

22. The method of claim 21, wherein the cancer is carcinoma of the bladder, uterine cervix, stomach, breast, lung, colon, rectum, or pancreas.

23. A method of treating cancer in a human, the method comprising administering to the human a population of host cells in an amount effective to treat cancer in the human,
   wherein the population of host cells expresses an isolated or purified nucleic acid and the cancer expresses HLA-A1 and KK-LC-$1_{52-60}$,
   wherein the nucleic acid comprises a nucleotide sequence encoding a TCR, wherein the TCR has antigenic specificity for KK-LC-$1_{52-60}$ presented by HLA-A1, and
   wherein the TCR comprises the amino acid sequences of SEQ ID NOs: 3-8.

24. The method of claim 23, wherein the cancer is carcinoma of the bladder, uterine cervix, stomach, breast, lung, colon, rectum, or pancreas.

25. An isolated or purified TCR encoded by the nucleic acid according to claim 4.

26. An isolated or purified nucleic acid comprising a nucleotide sequence encoding a TCR, wherein the TCR has antigenic specificity for KK-LC-$1_{52-60}$ presented by HLA-A1, and
   wherein the TCR comprises the amino acid sequences of SEQ ID NOs: 3-8 and a murine constant region.

* * * * *